(12) United States Patent
Zhao et al.

(10) Patent No.: US 10,772,488 B2
(45) Date of Patent: Sep. 15, 2020

(54) SYSTEM AND METHODS FOR ENDOSCOPIC IMAGING

(71) Applicant: Endoluxe Inc., Allentown, PA (US)

(72) Inventors: Philip Zhao, Fort Lee, NJ (US); Neal Patel, Duluth, GA (US)

(73) Assignee: Endoluxe Inc., Allentown, PA (US)

( * ) Notice: Subject to any disclaimer, the term of this patent is extended or adjusted under 35 U.S.C. 154(b) by 340 days.

(21) Appl. No.: 15/809,253

(22) Filed: Nov. 10, 2017

(65) Prior Publication Data

US 2019/0142256 A1 May 16, 2019

(51) Int. Cl.
*A61B 1/04* (2006.01)
*A61B 1/06* (2006.01)
(Continued)

(52) U.S. Cl.
CPC ........ *A61B 1/0638* (2013.01); *A61B 1/00016* (2013.01); *A61B 1/00029* (2013.01);
(Continued)

(58) Field of Classification Search
CPC ............ A61B 1/00052; A61B 1/00066; A61B 1/00068; A61B 1/00105; A61B 1/00115; A61B 1/00114; A61B 1/00112; A61B 1/00121; A61B 1/00124; A61B 1/00126; A61B 1/00128; A61B 1/00119; A61B 1/00163; A61B 1/00165; A61B 1/00167; A61B 1/0016; A61B 1/0017; A61B 1/00172; A61B 1/00177; A61B 1/00179; A61B 1/00181; A61B 1/00183;
(Continued)

(56) References Cited

U.S. PATENT DOCUMENTS 4,478,212 A 10/1984 Asano
5,311,859 A * 5/1994 Monroe ................. A61B 1/042
348/75
(Continued)

FOREIGN PATENT DOCUMENTS

WO WO2015191954 12/2015

OTHER PUBLICATIONS

International Search Report and Written Opinion dated Jan. 17, 2019 in related PCT Application No. PCT/US18/58357 filed Oct. 31, 2018 (13 pages).
(Continued)

*Primary Examiner* — Matthew J Kasztejna
(74) *Attorney, Agent, or Firm* — Dentons US LLP

(57) ABSTRACT

A portable endoscopic inspection system comprises an endoscope having a proximal end with a flanged eyepiece for observation and a distal end with a lens assembly for insertion into a region of interest. A light port transports incident light to the region of interest along an lighting pathway, and reflected light is transported along an imaging pathway from the lens assembly to the eyepiece. A wireless imaging unit comprises a light source which detachably couples to the light port for generating the incident light, and an imaging sensor for recording images of the reflected light from the eyepiece. The wireless imaging unit comprises a variable coupling system which mechanically couples the imaging sensor to the flanged eyepiece independent of the shape and/or size of the flange of the eyepiece.

26 Claims, 17 Drawing Sheets

(51) Int. Cl.
  *A61B 1/05* (2006.01)
  *A61B 1/00* (2006.01)
  *H04N 5/225* (2006.01)

(52) U.S. Cl.
  CPC ...... *A61B 1/00034* (2013.01); *A61B 1/00039* (2013.01); *A61B 1/00045* (2013.01); *A61B 1/00052* (2013.01); *A61B 1/00108* (2013.01); *A61B 1/00128* (2013.01); *A61B 1/042* (2013.01); *A61B 1/043* (2013.01); *A61B 1/053* (2013.01); *A61B 1/0669* (2013.01); *H04N 5/2252* (2013.01); *H04N 5/2253* (2013.01); *H04N 5/2256* (2013.01); *A61B 1/00195* (2013.01); *H04N 2005/2255* (2013.01)

(58) Field of Classification Search
  CPC . A61B 1/0086; A61B 1/0019; A61B 1/00195; A61B 1/00197; A61B 1/0638
  See application file for complete search history.

(56) References Cited

U.S. PATENT DOCUMENTS

| | | | |
|---|---|---|---|
| 5,808,813 | A | 9/1998 | Lucey et al. |
| 5,822,546 | A | 10/1998 | George |
| 6,646,866 | B2 | 11/2003 | Kao |
| 6,657,654 | B2 | 12/2003 | Narayanaswami |
| 7,442,167 | B2 * | 10/2008 | Dunki-Jacobs ...... A61B 1/0653 600/129 |
| 7,986,342 | B2 | 7/2011 | Yogesan et al. |
| 8,029,439 | B2 * | 10/2011 | Todd ............. A61B 1/0653 362/572 |
| 8,604,753 | B2 | 12/2013 | Bessa et al. |
| 8,711,552 | B2 | 4/2014 | Medica et al. |
| D710,856 | S | 8/2014 | Daniel |
| 8,928,746 | B1 | 1/2015 | Stevrin et al. |
| 8,944,596 | B2 | 2/2015 | Wood et al. |
| 10,051,166 | B2 * | 8/2018 | Duckett, III ......... A61B 1/0669 |
| 2002/0103420 | A1 | 8/2002 | Coleman et al. |
| 2003/0050534 | A1 | 3/2003 | Kazakevich |
| 2003/0227746 | A1 | 12/2003 | Sato |
| 2005/0191046 | A1 * | 9/2005 | Dehmel ............. A61B 1/042 396/17 |
| 2006/0116550 | A1 | 6/2006 | Noguchi et al. |
| 2008/0104300 | A1 | 5/2008 | Diener et al. |
| 2008/0183910 | A1 | 7/2008 | Natoli et al. |
| 2009/0012361 | A1 | 1/2009 | MacKinnon et al. |
| 2010/0145146 | A1 | 6/2010 | Melder |
| 2010/0198009 | A1 | 8/2010 | Farr et al. |
| 2010/0279418 | A1 | 11/2010 | Larson et al. |
| 2011/0015496 | A1 | 1/2011 | Sherman et al. |
| 2011/0055447 | A1 | 3/2011 | Costa |
| 2011/0195753 | A1 | 8/2011 | Mock et al. |
| 2012/0077552 | A1 | 3/2012 | Bessa et al. |
| 2012/0106037 | A1 | 5/2012 | Diebel et al. |
| 2012/0162401 | A1 | 6/2012 | Melder et al. |
| 2012/0225622 | A1 | 9/2012 | Kudrna et al. |
| 2012/0320340 | A1 | 12/2012 | Coleman |
| 2013/0083185 | A1 | 4/2013 | Coleman |
| 2013/0096378 | A1 | 4/2013 | Alexander et al. |
| 2013/0102359 | A1 | 4/2013 | Ho |
| 2013/0262730 | A1 | 10/2013 | Al-Ali et al. |
| 2013/0281155 | A1 | 10/2013 | Ogata et al. |
| 2013/0344917 | A1 | 12/2013 | Sobti et al. |
| 2014/0038222 | A1 | 2/2014 | Alt et al. |
| 2014/0051923 | A1 | 2/2014 | Mirza et al. |
| 2014/0073969 | A1 | 3/2014 | Zou et al. |
| 2014/0107416 | A1 | 4/2014 | Birnkrant |
| 2014/0140049 | A1 | 5/2014 | Cotelo |
| 2014/0142390 | A1 | 5/2014 | Bromwich |
| 2014/0170761 | A1 | 6/2014 | Crawford et al. |
| 2014/0200054 | A1 | 7/2014 | Fraden |
| 2014/0210977 | A1 | 7/2014 | Amling et al. |
| 2014/0249405 | A1 | 9/2014 | Wimer |
| 2014/0364711 | A1 | 12/2014 | Ismail et al. |
| 2015/0002606 | A1 | 1/2015 | Hyde et al. |
| 2015/0073285 | A1 | 3/2015 | Albert et al. |
| 2015/0112141 | A1 | 4/2015 | Storz |
| 2015/0362828 | A1 | 12/2015 | Patel et al. |
| 2017/0099479 | A1 | 4/2017 | Browd et al. |
| 2017/0273539 | A1 * | 9/2017 | Law ............... A61B 1/0669 |
| 2019/0167074 | A1 * | 6/2019 | Malinskiy ......... A61B 1/00108 |

OTHER PUBLICATIONS

International Search Report and Written Opinion dated Sep. 18, 2015 in related PCT Application No. PCT/US15/35479 filed Jun. 12, 2015 (7 pages).

* cited by examiner

SYSTEM AND METHODS FOR ENDOSCOPIC IMAGING

TECHNICAL FIELD

This disclosure relates to systems, apparatuses, and methods utilizing an endoscopic imaging system. More specifically, this disclosure relates to wireless transmission of an endoscopic image from a portable device to a remote display or remote storage.

BACKGROUND

Endoscopy in a medical field permits internal features of a body of a patient to be inspected without a use of a traditional, fully-invasive surgery. An endoscope typically comprises a system of lens at a distal end which transmits an image through an optical pathway housed within a flexible tube to an eye piece at a proximal end. A clinician can use the eye piece to inspect the internal features at the distal end or the eye piece can be coupled to an imaging system. The imaging system generally includes a camera coupled to the eye piece that transmits a digital image data to display device over a physical cable. High intensity light is provided at the distal end of the endoscope by an external light source. This light source is coupled to a light port, situated near the proximal end, by the eye piece, and transmitted to the distal end via an optical pathway such as an optical fiber.

Endoscopic systems are typically expensive and complicated due to their specialized equipment and need for sterility in medical applications. The endoscope uses fiber optics for image and light transmission. The image is usually transmitted and processed through an expensive and complex image-processing unit that then displays the image on a separate display, such as a video screen. This collection of images and video processing units and displays are usually bulky and not mobile, and thus not practical in emergent use or in areas of world were such equipment are cost prohibitive. Furthermore, using an external video capture or screening device usually requires bulky monitors, external cabling and external power. Similarly, a typical endoscope light source is remote to the endoscope and must be connected via a fiber-optic type cable from a source to the light port of the endoscope. This configuration limits movement and mobility of the endoscope.

A typical light source unit is comprised of a high intensity light source, such as an incandescent bulb or light emitting diode (LED), a dedicated optical cable, a ballast power supply, a set of control circuitry, and a cooling fan. These systems are expensive, complicated, and inefficient. Also, these systems must compensate for losses along the light conduit, monitor for hazardous conditions for patient caused by infrared heat, while allowing for a mechanical control of a color content of a light, which can adversely affect image quality, especially when a dedicated light cable that connects the light source to the endoscope is cumbersome.

Accordingly, there exists a need for an inexpensive, lightweight, mobile platform that is both accurate and reliable, and does not require an excessive amount of time to assemble or to establish external connections or cables.

SUMMARY

According to one embodiment, a portable endoscopic inspection system is presented. The portable endoscopic system includes an endoscope having a proximal end which has a flanged eyepiece for observation and a handle; a distal end which is for insertion into a region of interest; a lens assembly housed within the distal end; a light port; an illumination pathway which optically couples the light port and the lens assembly to transport incident light to the region of interest; and an imaging pathway which optically couples the eyepiece and lens assembly for transporting the reflected light from the region of interest to the flanged eyepiece. The portable endoscopic inspection system also includes a wireless imaging unit which comprises a housing; a light source assembly which detachably couples to the light port for generating the incident light; an imaging sensor for recording images of the reflected light from the eyepiece; and a variable coupling system which mechanically couples the imaging sensor to the flanged eyepiece independent of the shape and/or size of the flange.

In another embodiment, wherein the variable coupling system comprises sensor optics which focuses the reflected light from the flanged eyepiece onto the imaging sensor; and a biasing member which biases the sensor optics directly against the eyepiece.

In another embodiment, wherein the variable coupling system further includes at least one circumferential roller bearing which mechanically engages the flanged eyepiece to the variable coupling system in order to directly couple the sensor optics with the flanged eyepiece; and an outer sleeve which translates bi-directionally in a lateral direction to selectively disengage the roller bearing from the flanged eyepiece.

In another embodiment, wherein the outer sleeve surrounds the sensor optics and imaging sensor.

In another embodiment, wherein the roller bearing generates an engagement force opposite to the biasing member in order to axially align the sensor lens and the eyepiece.

In another embodiment, wherein the eyepiece flange has a major width of 30 mm to 40 mm.

In another embodiment, wherein the wireless imaging unit further comprises a recess in the housing for magnetically receiving the light source assembly.

In another embodiment, wherein the wireless imaging unit further comprises a ferromagnetic adapter which attaches to the light port and magnetically couple the light source assembly to the light port.

In another embodiment, wherein the light source assembly further includes a heat sink to dissipate heat away from a light source.

In another embodiment, wherein the light source assembly further comprises a multispectral light source; and a light guide which optically couples the light source to the illumination pathway.

In another embodiment, wherein the multispectral light source includes a plurality of light emitting diodes, each capable of outputting a selected wavelength.

In another embodiment, wherein the multispectral light source is capable of at least one of narrow band imaging, auto-fluorescence imaging, and white light imaging.

In another embodiment, wherein the multispectral light source is capable of selectively outputting a range of wavelengths from 365 nm to 540 nm.

In another embodiment, wherein the wireless imaging unit further includes at least one wireless transceiver for wirelessly transmitting the recorded images.

In another embodiment, wherein the wireless imaging unit further includes at least two wireless transceivers for wirelessly transmitting the recorded images from each wireless transceiver substantially simultaneously.

In another embodiment, the system further comprising at least one wireless receiver for receiving the wirelessly transmitted recorded images.

In another embodiment, the system further comprising a docking station with at least one wireless receiver for receiving the wirelessly transmitted recorded images.

In another embodiment, wherein the docking station further includes an inductive element for wirelessly transmitting power to a rechargeable battery which supplies power to the wireless imaging unit.

In another embodiment, wherein the docking station further includes a video output port for transmitting wirelessly received images to a display unit.

In another embodiment, wherein the wireless imaging unit further includes an image control unit which controls: (a) the image sensor to record the images from the eyepiece and (b) the light source assembly to produce the incident light which illuminates the region of interest.

In another embodiment, wherein the image control unit controls an autofocus driver to adjust the focal length between the imaging sensor and the sensor optics.

In another embodiment, wherein the wireless imaging unit further includes an image processing unit which receives analog signals from individual pixels of the imaging sensor which correspond to the recorded images, converts the analog signals to digital signals, and stores a corresponding digital image to an image memory.

In another embodiment, wherein the image processing unit comprises an image enhancement unit which adjusts individual pixels values of the stored digital image according a selected image processing algorithm.

In another embodiment, wherein the image processing algorithm is selected from color enhancement, greyscale enhancement, contour enhancement, pattern recognition, feature extraction, digital filtering, and any combination thereof.

In another embodiment, wherein the image processing unit comprises a post-processing unit which encodes the stored digital images for wireless transmission.

In another embodiment, further comprising an elongated flexible tube extending from the handle to the distal end which houses the at least the imaging pathway and the illumination pathway.

In another embodiment, a method for performing an endoscopic examination is presented. The method includes attaching a wireless imaging unit to a flanged eyepiece of an endoscope with a variable coupling system which mechanically couples the imaging sensor to the flanged eyepiece independent of the shape and size of the flange; attaching a light source assembly to a light port of the endoscope which receives incident light generated by the light source assembly; inserting a distal end of the endoscope into a region interest; transporting incident light from a light port along an illumination pathway to a lens assembly housed within the distal end; transporting reflected light from the region of interest from the lens assembly along an imaging pathway to the flanged eyepiece; and recording images from the flanged eyepiece with an imaging sensor.

In another embodiment, the method further including focusing the reflected light from the eyepiece onto the imaging sensor with sensor optics disposed therebetween; and biasing the sensor optics directly against the flanged eyepiece with a biasing member.

In another embodiment, the method further including mechanically engaging the flanged eyepiece with at least one circumferential roller bearing of the variable coupling system in order to directly couple the sensor optics with the flanged eyepiece; and selectively disengaging the roller bearing from the flanged eyepiece by translating an outer sleeve in either lateral direction.

In another embodiment, wherein the outer sleeve surrounds the sensor optics and imaging sensor.

In another embodiment, wherein the roller bearing generates an engagement force opposite to the biasing member in order to axially align the sensor lens and the eyepiece.

In another embodiment, wherein the eyepiece flange has a major width of 30 mm to 40 mm.

In another embodiment, the method further including stowing the light source assembly into a recess of the wireless imaging unit housing using a ferromagnetic coupling.

In another embodiment, the method further including magnetically coupling a ferromagnetic adapter releasably attached to the light port to the light source assembly.

In another embodiment, the method further including dissipating heat away from a light source with a thermally coupled heatsink of the light source assembly.

In another embodiment, the method further including generating a multispectral incident light with a multispectral light source.

In another embodiment, wherein the multispectral light source includes a plurality of light emitting diodes, each capable of outputting a selected wavelength.

In another embodiment, wherein the multispectral light source is capable of at least one of narrow band imaging, auto-fluorescence imaging, and white light imaging.

In another embodiment, wherein the multispectral light source is capable of selectively outputting a range of wavelengths from 365 nm to 540 nm.

In another embodiment, the method further including wirelessly transmitting the recorded images with at least one wireless transceiver.

In another embodiment, the method further including wirelessly transmitting the recorded images with at least two wireless transceivers substantially simultaneously.

In another embodiment, the method further including wirelessly receiving the wirelessly transmitted recorded images with at least one wireless receiver.

In another embodiment, the method further including wirelessly transmitting power to a rechargeable battery which supplies power to the wireless imaging unit.

In another embodiment, the method further including outputting the wirelessly received recorded images to display unit.

In another embodiment, the method further including receiving analog signals from individual pixels of the imaging sensor; converting the analog signals to digital signals; and storing a corresponding digital image to an image memory.

In another embodiment, the method further including adjusting individual pixel values of stored digital image according a selected image processing algorithm; and encoding the stored digital images for wireless transmission.

In another embodiment, a kit for a portable endoscopic inspection system is presented. The kit includes an endoscope having a proximal end with a flanged eyepiece for observation and a handle; a distal end for insertion into a region of interest; a lens assembly housed within the distal end; a light port; an illumination pathway which optically couples the light port and the lens assembly to transport incident light to the region of interest; and an imaging pathway which optically couples the eyepiece and lens assembly for transporting the reflected light from the region of interest to the flanged eyepiece. The kit also includes a wireless imaging unit which comprises a housing; a light source assembly detachably coupled to the light port for generating the incident light; an imaging sensor for recording images of the reflected light from the eyepiece and a variable coupling system which mechanically couples the imaging sensor to the flanged eyepiece independent of the shape and/or size of the flange. Furthermore, the kit includes a plurality of light port adapters, each of which having a central channel of varying diameter, wherein each light port adapter receives the light port at one end and magnetically couples to the light source assembly at an opposite end.

DETAILED DESCRIPTION

Figure 1:
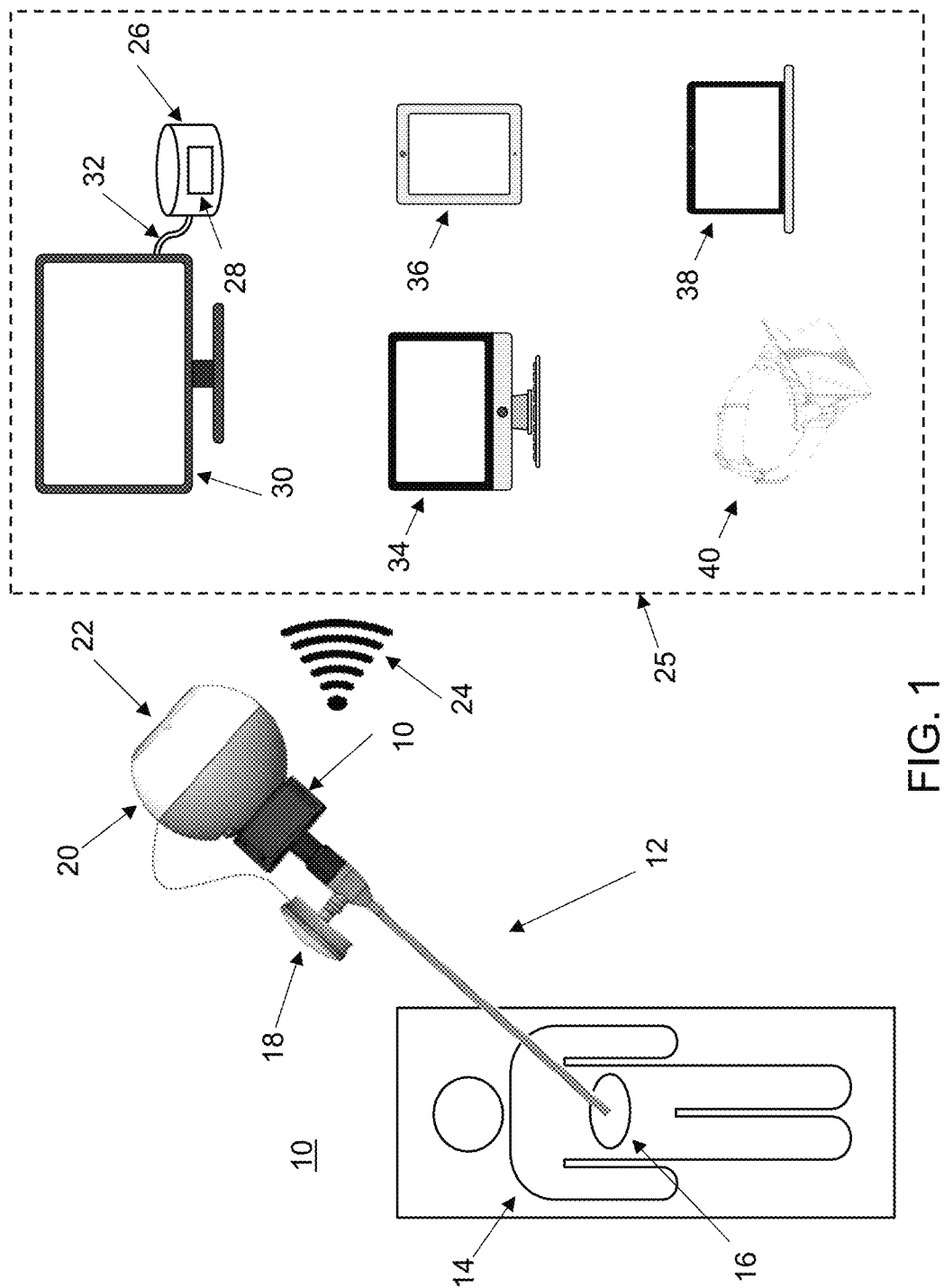
FIG. 1 is a structural diagram which shows a construction of a portable endoscopic inspection system and related external devices of a local area network according to an embodiment of this disclosure.

Hereinafter, various embodiments of this disclosure will be further described in more detail with reference to various accompanying drawings so that the this disclosure may be readily implemented by skilled artisans. However, one should note that this disclosure is not limited to the embodiments disclosed herein, but is capable of being embodied or carried out in various other ways. In drawings, some parts irrelevant to description are omitted for simplicity of explanation, and like reference numerals can denote like parts through this disclosure.

In this disclosure, a term "connected to" or "coupled to" that is used to designate a connection or coupling of one element to another element includes both a case that an element is "directly connected or coupled to" another element and a case that an element is "electronically connected or coupled to" another element via still another element (wireless). Further, in this disclosure, a term "comprises or includes" and/or "comprising or including" means that one or more other components, steps, operation and/or existence or addition of elements are not excluded in addition to various described components, steps, operation and/or elements unless context dictates otherwise.

Terms and words used in this disclosure and claims are not to be construed as a general or dictionary meaning, but are to be construed to meaning and concepts meeting various technical ideas of this disclosure based on a principle that inventor can appropriately define various concepts of terms in order to describe their own inventions in best mode.

Various features and aspects of this disclosure can be best understood by reference to various accompanying drawings, when considered during in light of below.

FIG. 1 shows a set of main components of a portable inspection system 10 used during an endoscopic examination according to an embodiment of this disclosure. An endoscope 12 is inserted into a patient 14 using a portable inspection system 10 to inspect a region of interest 16, such an organ or biological tissue or in vivo. The region of interest 16 is illuminated by an external light source 18, which directs incident light along an illumination pathway such as an optical fiber which extends along a tube of the endoscope 12 to an illumination lens at a distal end. The illuminated region of interest 16 reflects the incident light back to an imaging lens at the distal tip to convey the reflected light along an imaging pathway, such as an optical fiber. The reflected light is received by a wireless imaging unit 20, which includes a digital imaging sensor that converts the reflected light into a digital image, which can displayed on a touchscreen display unit 22 or another form of display, whether, which may be haptic or non-touch-enabled. For example, this form of display can include an LED display, a plasma display an electrophoretic display, a holographic display, or others. Note that the patient 14 can be a mammal, such as a human or others.

The imaging unit 20 is capable of high speed wireless bi-directional data communication 24 to one or more of external devices 25 simultaneously or substantially simultaneously. The external devices 25 are capable of directly receiving data, such as digital images, digital video, or other information pertaining to an endoscopic examination. The external device 25 can also directly transmit data to the imaging unit 20, such as control signals to remotely control the imaging unit 20 and information regarding the endoscopic examination, such as patient data in a form of electronic medical records (EMR). One external device 25 is a docking station 26, which is capable of displaying the digital images on an integrated display unit 28 or on an external display 30, such as a television or display monitor, which is connected via a display cable 32. Another external device 25 includes personal computer devices, such as desktop computers 34; portable devices 36, such as smart devices, smart phones, personal digital assistants, tablet computers, wrist mounted displays, smart watches, or others; laptops or portable computers 38; head mounted displays 40; or other personal computing devices developed in future not yet contemplated.

Figure 2:
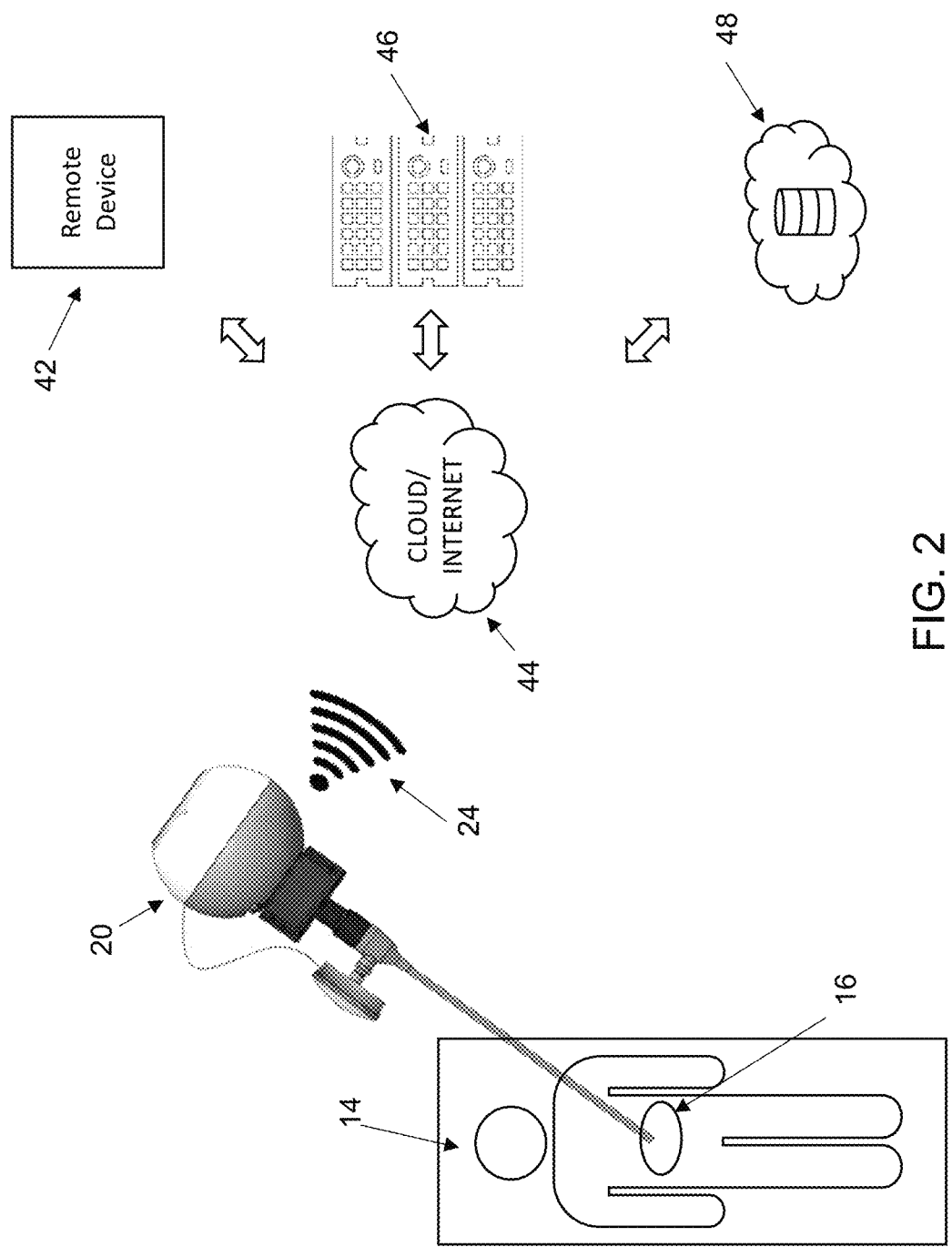
FIG. 2 is a structural diagram which shows a construction of a portable endoscopic inspection system and related external devices over a wide area network according to an embodiment of this disclosure.

With reference to FIG. 2, in another embodiment, the imaging unit 20 is capable of wireless communication 24 to a plurality of remote devices 42 indirectly over a cloud connection or Internet connection 42 for remote viewing of the endoscopic images, video, or examination data and for remotely receiving controls and/or EMR data. Note that this connection can be any type of network, such as a local area network (LAN, a wide area network (WAN), or others, whether encrypted or unencrypted. EMR data can include a collection of patient and population health information electronically stored in a digital format. EMR data may include a range of patient information, such as demographics, medical history, medication and allergies, immunization status, laboratory test results, radiology images, vital signs, personal statistics like age and weight, and billing information. EMR data can be stored on a health institution server 46 such as those located at a hospital, insurance company, government entity, remote data center, or others. EMR data can be stored on cloud storage system 48. The cloud storage system 48 can be a data storage system where the digital EMR data is stored in logical pools wherein the physical storage spans multiple servers and often locations in a distributed fashion in order to ensure redundancy, fault tolerance, durability of data. Institution server 46 and cloud storage 48 can include a picture archiving and communication system (PACS) which is capable of providing storage and access to medical images from multiple modalities using a universal image format such as Digital Imaging and Communications in Medicine (DICOM) format.

One should note that institution server 46 and cloud storage 48 can be compliant with data protection and privacy regulation, such as Health Insurance Portability and Accountability Act (HIPAA) in United States of America, General Data Protection Regulation (GDPR) in European Union, Personal Information Protection and Electronic Documents Act (PIPEDA) in Canada, National Health Portal compliance set by Insurance Regulatory and Development Authority of India (IRDAI), or other compliance regulations mandated globally.

Figure 3:
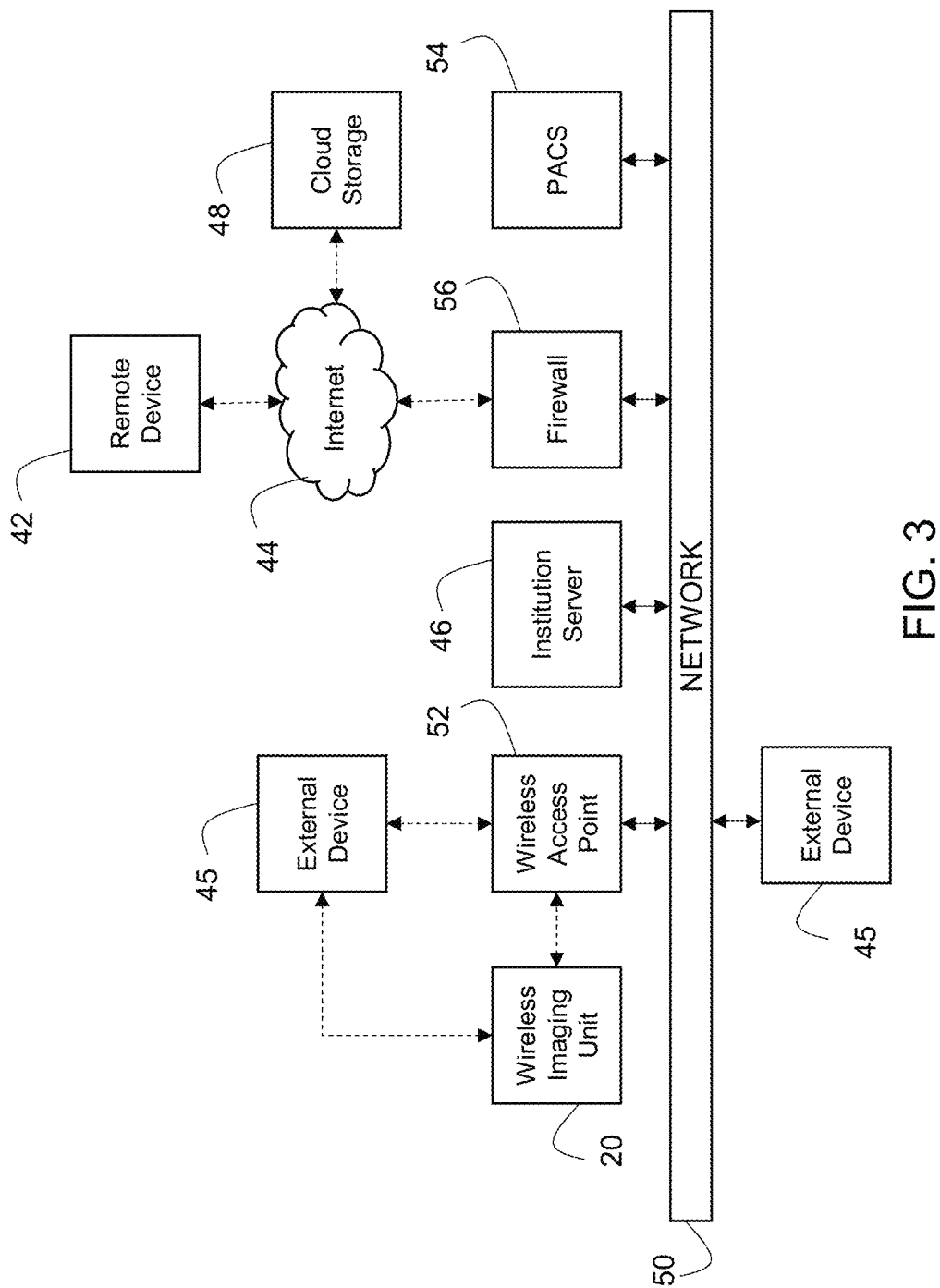
FIG. 3 is a block diagram of a communication network utilized by a portable endoscopic inspection system according to an embodiment of this disclosure.

With reference to FIG. 3, an embodiment of a portable inspection system 10 is depicted. The wireless imaging unit 20 is wirelessly coupled to a local network 50 via a wireless access point 52 using a suitable wireless transmission protocol such as the 802.11 family of modulation techniques, IEEE 802.15.4a ultra-wideband (UWB), and the like (Bluetooth). The local network 50 may include cables, switches, and routers which may utilize Ethernet standards for communication. At least one institution server 46 maybe in communication with the local network 50. For example, the institution server 46 may store or have access to EMR data which maybe access by the wireless imaging unit 20. Additionally, the local network 50 may be attached to a picture archiving and communication system (PACS) 54 which may communication with the institution server 46 and the wireless imaging unit 20. At least one external device 45 is coupled to the local network either directly via a physical connection or wirelessly via the wireless access point 52 and in some embodiments optically via a waveguide. In addition, a firewall 56 or other network security technology maybe connected to the local network 50 to control access to the Internet 44. For example, an authorized remote device 42 may access the local network 50 via a WAN, such as Internet 44, utilizing a secure connection facilitated by the firewall 56. In addition, the cloud storage system 48 to store or retrieve data may be accessed via the WAN, which is facilitated by the firewall 56.

Figure 4:
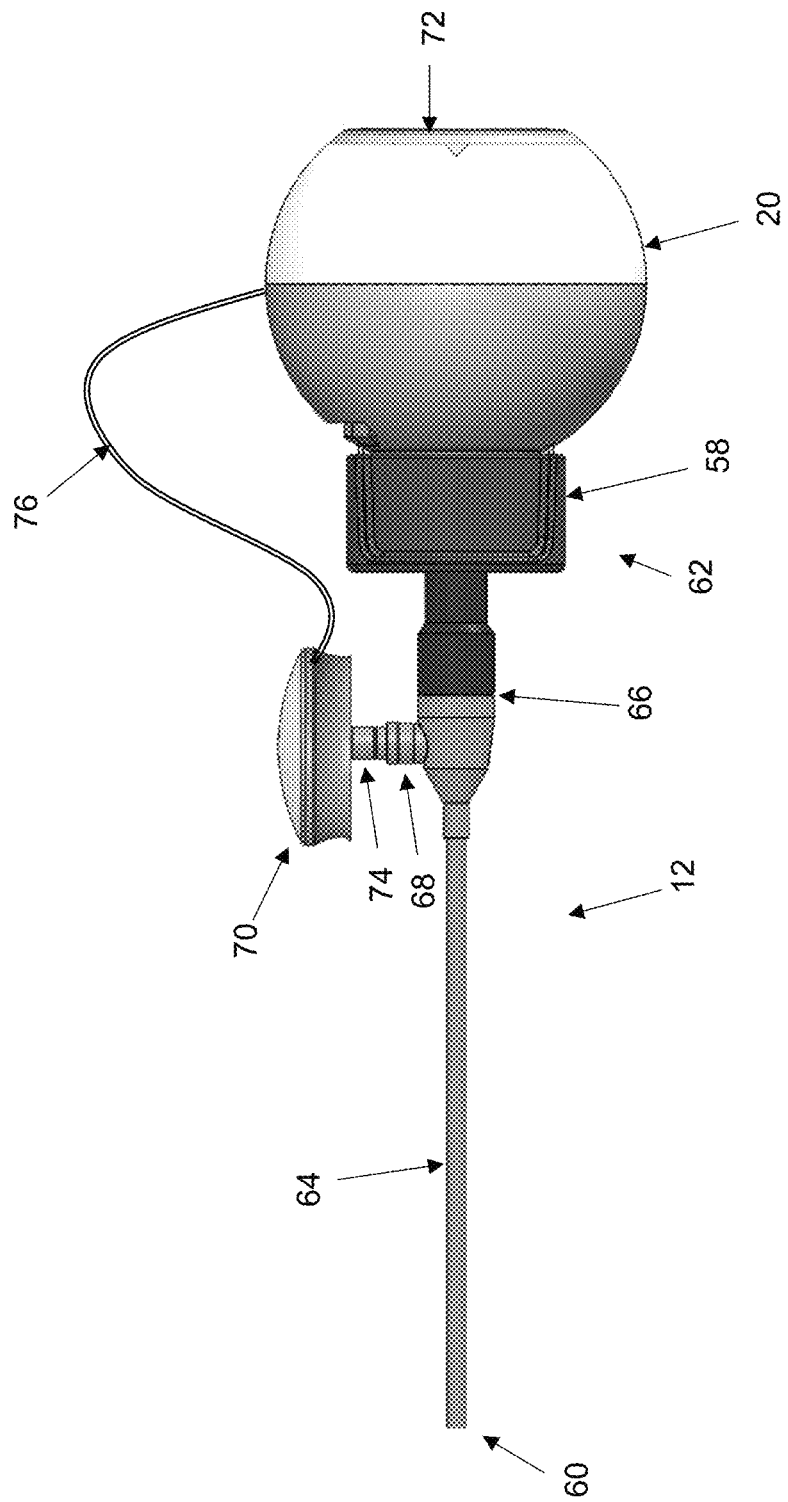
FIG. 4 is a perspective view of a wireless imaging unit according to an embodiment of this disclosure.

With reference to FIG. 4, an embodiment of the endoscope 12 and the wireless imaging unit 20 coupled is depicted. The endoscope 12 includes a distal end 60, a proximal end 62, an elongate, flexible tube 64, and a handle 66. The tube 64 extends between the distal end 60 and the proximal end 62, while being adjacent to the handle 66. The endoscope 12 is detachably coupled to the portable imaging system 20 by a variable coupling system 58, which mechanically couples a distal end of the imaging system 20, which includes an imaging sensor, to an eye piece situated at the proximal end 62 of the endoscope 12. The distal end 60 houses an illumination lens, which is optically coupled to a light port 68 near the proximal end 62 through an illumination pathway. The light port 68 transmits a high intensity incident light from a light source assembly 70 to the illumination lens at the distal end 60 in order to illuminate a region of interest. The distal end 60 also houses an imaging lens, which is optically coupled to an eye piece through an optical pathway for transmitting an image from the region of interest to the eye piece at the proximal end 62. The image is based on the incident light from the light source assembly 70 reflected from the region of interest to the imaging lens. The imaging lens and illumination lens together form a lens assembly which is discussed in even further detail below. The images or video captured from the region of interest are then post-processed by the imaging unit 20 and can be display locally on a touchscreen display unit 72 or another form of display, whether touch-enabled or non-touch-enabled, such as haptic, holographic, electrophoretic, or others.

The light source assembly 70 is magnetically coupled to the light port 68 by way of a light port adapter 74. The light port adapter 74 attaches to the light port 68 by a screw mechanism, a friction fit, or other mechanical attachment method to securely couple one another. The light port adapter 74 is composed of a ferritic material in order to achieve the magnetic coupling. The light source assembly 70 is capable of outputting multi-frequency or multi-spectral light at varying intensities. The frequency and intensity of light is controlled by the wireless imaging unit 20, which sends control signals over a control cable 76.

Figure 5:
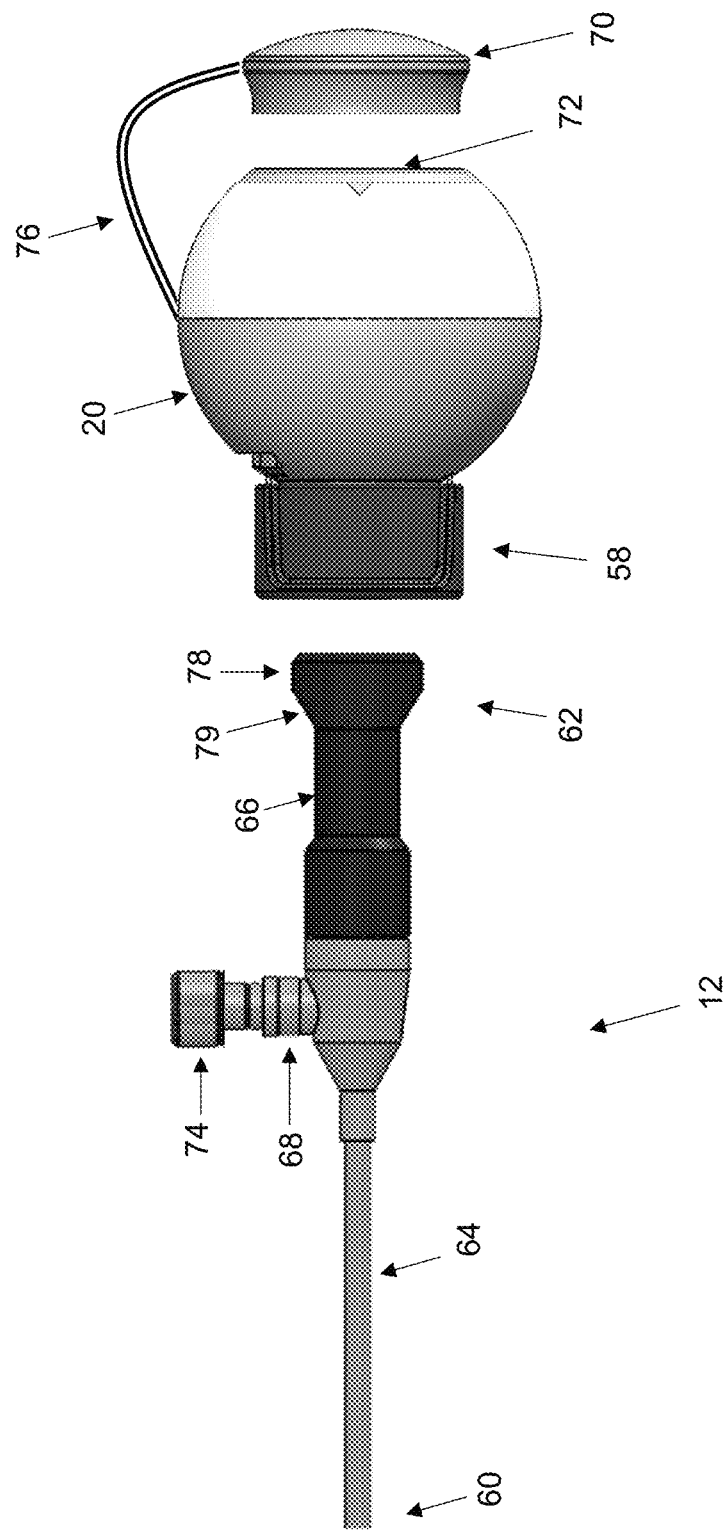
FIG. 5 is an exploded perspective view of a wireless imaging unit according to an embodiment of this disclosure.

With reference to FIG. 5, an embodiment of the endoscope 12 and the wireless imaging unit 20 uncoupled, such as unassembled, is depicted. At the proximal end 62 of the endoscope 12 is an eyepiece 78. The eyepiece 78 includes a flange 79 which can suitably vary in diameter, angle, and thickness as needed for the endoscope 12. For example, many of the endoscope 12 eyepieces 78 can be manufactured with a conventional C-mount coupling, which uses an industry standing 31.75 mm diameter eyepiece. However, due to manufacturing tolerances, a diameter can be slight larger or slightly smaller than the industry standard 31.75 mm, such as within about 20% range. Furthermore, a flange angle or a flange thickness may vary from manufacture to manufacture since there may be no industry standards governing these dimensions. Therefore, the variable coupling system 58 can accommodate slight differences in diameter, thickness, and flange angle of the eyepiece 78. The variable coupling system 58 is discussed in even further detail below.

Figure 6:
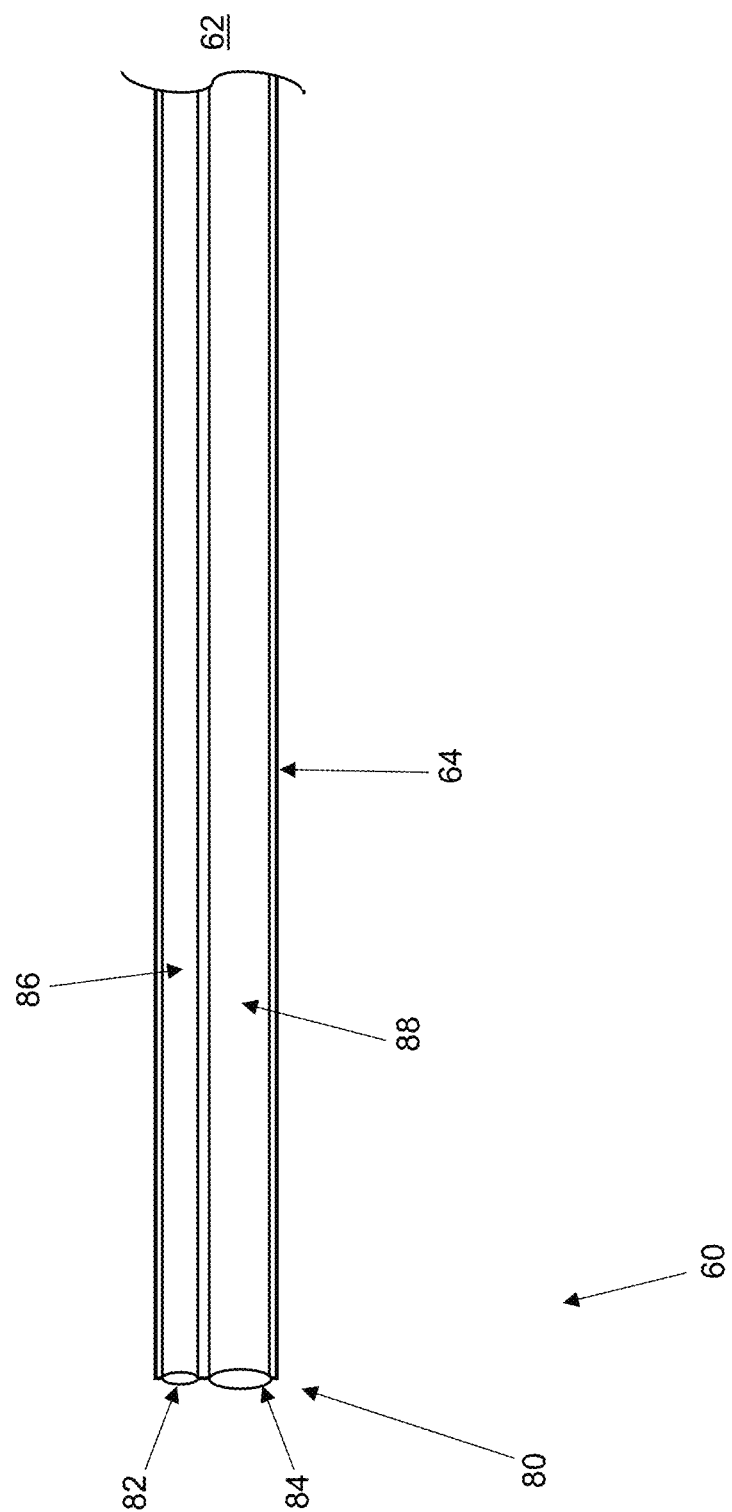
FIG. 6 is a cut away view of a distal end of an endoscope according to an embodiment of this disclosure.

With reference to an embodiment of FIG. 6, a close-up view of the distal end 24 of the endoscope 12 is depicted. At the distal end 24 of the flexible tube 64 is a lens assembly 80. The lens assembly 80 includes at least an illumination lens 82 and an imaging lens 84. As previously mentioned, the illumination lens 82 is optically coupled to the light source assembly 70 by an illumination pathway 86. The illumination pathway 86 can be a flexible optical fiber or any other optical transmission medium capable of transmitting the multispectral incident light from the light source assembly 70. The reflected light from the region of interest is collected by the imaging lens 84, which is optically coupled to eyepiece 78 by the imaging pathway 88, which also run along the flexible tube 64 and handle 66. The imaging pathway 88 can be a flexible optical fiber or any other optical transmission medium capable of transmitting the multispectral reflected light from the region of interest to the eyepiece 78.

Figure 7B:
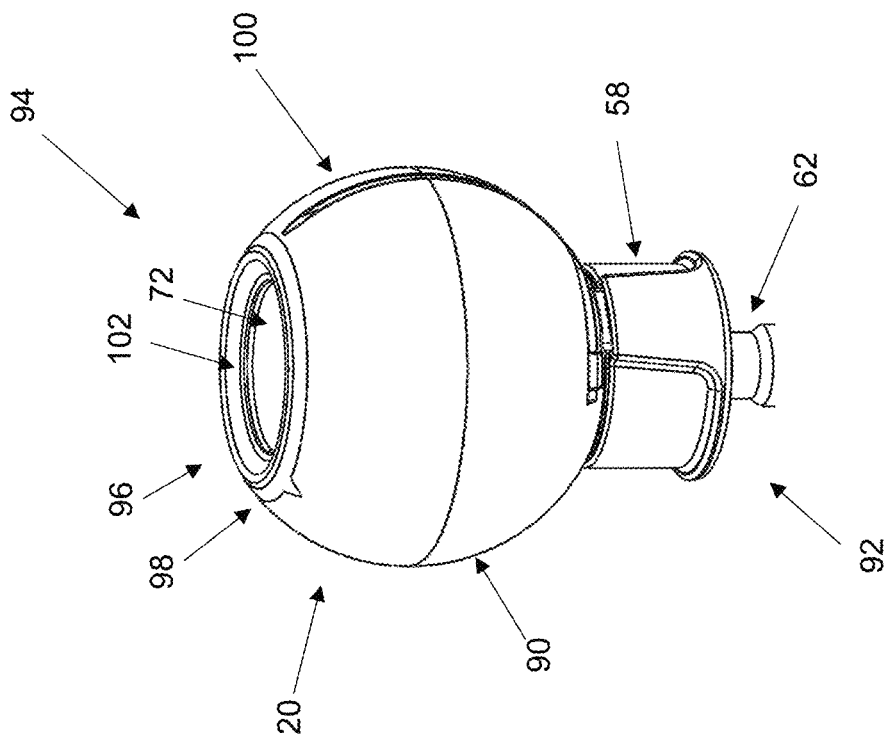
FIGS. 7A-7B are isometric views of a wireless imaging unit according to an embodiment of this disclosure.
Figure 7A:
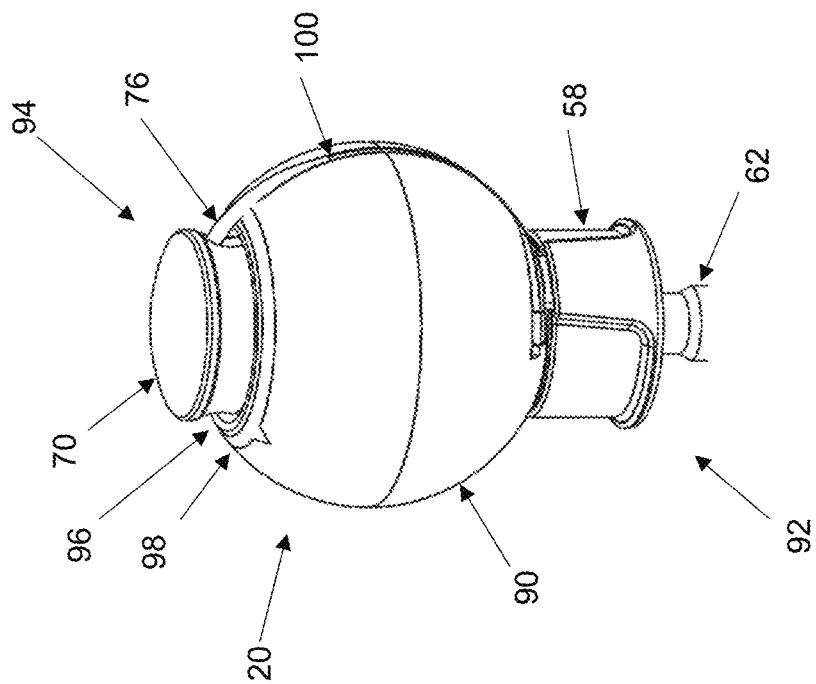

With reference to embodiments of both FIGS. 7A and 7B, a perspective view of the wireless imaging unit 20 coupled to the distal end 62 of the endoscope 12 is depicted in which a light source assembly 70 is in a docked and undocked configuration, respectively. The imaging unit 20 comprises a housing 90 which defines a distal end 92 and a proximal end 94. At the distal end 92 of the housing 90 is the variable clamping system 58, which mechanically couples the distal end 92 of the imaging unit 20 to the proximal end 94 of the wireless imaging unit 20. At the proximal end 94 of the housing 90 is a circular recess 96 for ferromagnetically receiving a light source assembly. A bezel 98 is defined at an outer edge of the circular recess 96 where the housing 90 meets the circular recess 96. When the light source assembly 70 is in the docked configuration, there is a cable channel 100 in the housing 90 for stowing the control cable 76 substantially flush with an external profile of the housing 90. The channel 100 ensures that the control cable 76 can safely secured and mitigates potential damage during transport or storage when the portable inspection system 10 is not in use. When in the docked state, the light source assembly 70 also covers the touchscreen display unit 72 and acts as a protective cover.

When the light source assembly 70 is in an undocked state, the touchscreen display unit 72 is uncovered as well as a light ring 102 is composed of a ferritic material to accommodate the ferromagnetic coupling between the light source assembly 70 and the housing 90. The light right 102 also includes a hall effect sensor, which detects whether the light source assembly 70 is in a docked or undocked state. When in a docked state as shown in FIG. 7A, the hall effect sensor signals a controller, which controls the wireless imaging unit 20 to turn off or place the wireless imaging unit 20 in low power standby mode. When in an undocked state as shown in FIG. 7B, the hall effect sensor signals a controller to turn on the wireless imaging unit 20 and the user is presented with a user interface on the touchscreen display unit 72 to control the wireless imaging unit 20.

Figure 8:
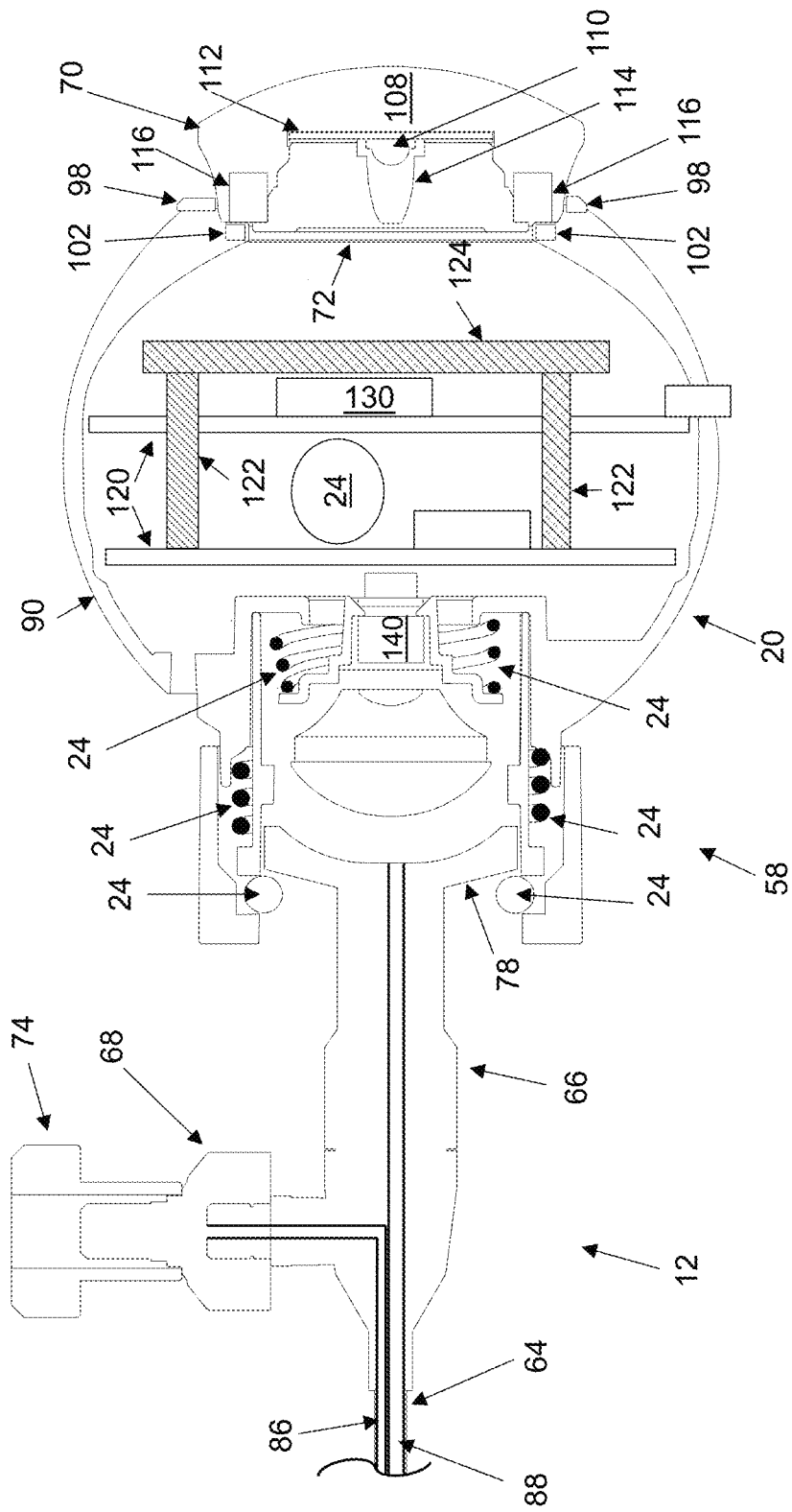
FIG. 8 is a cross-sectional view of a wireless imaging unit according to an embodiment of this disclosure.

With reference to an embodiment of FIG. 8, a cut away view of the wireless imaging unit 20 coupled to the endoscope 12 with the light source assembly 70 in a docked state is depicted. At the proximal end 94 of the imaging unit 20, the light source assembly 70 is in a docked state. The light source assembly 70 includes a housing 108, which houses a high intensity multispectral light source 110 which is mounted on a light source printed circuit board (PCB) 112 which includes various electronic components for receiving various control signals from the imaging unit 20 and for controlling an intensity and a frequency or frequencies of an incident light generated by the light source 110.

The light source PCB 112 is thermally coupled to the housing 108 by a thermal interface material, which acts to transmit heat generated by the light source PCB 112 to the housing 108. The housing 108 can be constructed of a thermally conductive material, such as aluminum, a magnesium alloy, a titanium alloy, or any other suitable material with a high thermal conductivity to act as a heatsink for the light source 110 and light source PCB 112. The heatsink housing 108 protects light source 110 and light source PCB 112 from overheating allowing an endoscopic procedure to continue for an extended duration without risking thermal damage to electronics or the light source 110.

The light source 110 is covered by and optically coupled to an illumination lens 114. The illumination lens 114 directs, focuses, and optically couples an incident light from the light source 110 to the illumination pathway 86. The light source 110 includes a single light emitting diode (LED) or a plurality of LEDs each having a different spectral or frequency output. The plurality of LEDs are each individually controlled or tuned to put the desired frequency or frequencies of incident light. For example, the LEDs can be narrow band LEDs capable of outputting at least one frequency within the range of 365 nm to 540 nm or multiple frequencies within that range. The multispectral light source 110 is also capable of outputting frequencies of light required for auto-fluorescence imaging and white light imaging. Control signals for controlling the intensity of each LED within the multispectral light source 110 are sent over the control cable 76 from the imaging unit 20. Using a user interface displayed on the touchscreen display unit 72, in an external device 45, or on a remote device 45, a user can select which imaging frequencies are output from the multispectral light source 110 during an endoscopic procedure.

The light source housing 108 includes a ferromagnetic ring 116 which magnetically couples the light source assembly 70 to the light ring 102. As previously mentioned, when the ferromagnetic ring 116 comes in contact with the light ring 102, a hall effect sensor in the light ring 102 detects the presence of a magnetic field and sends a signal to the controller to turn off the wireless imaging unit 20.

Figure 9:
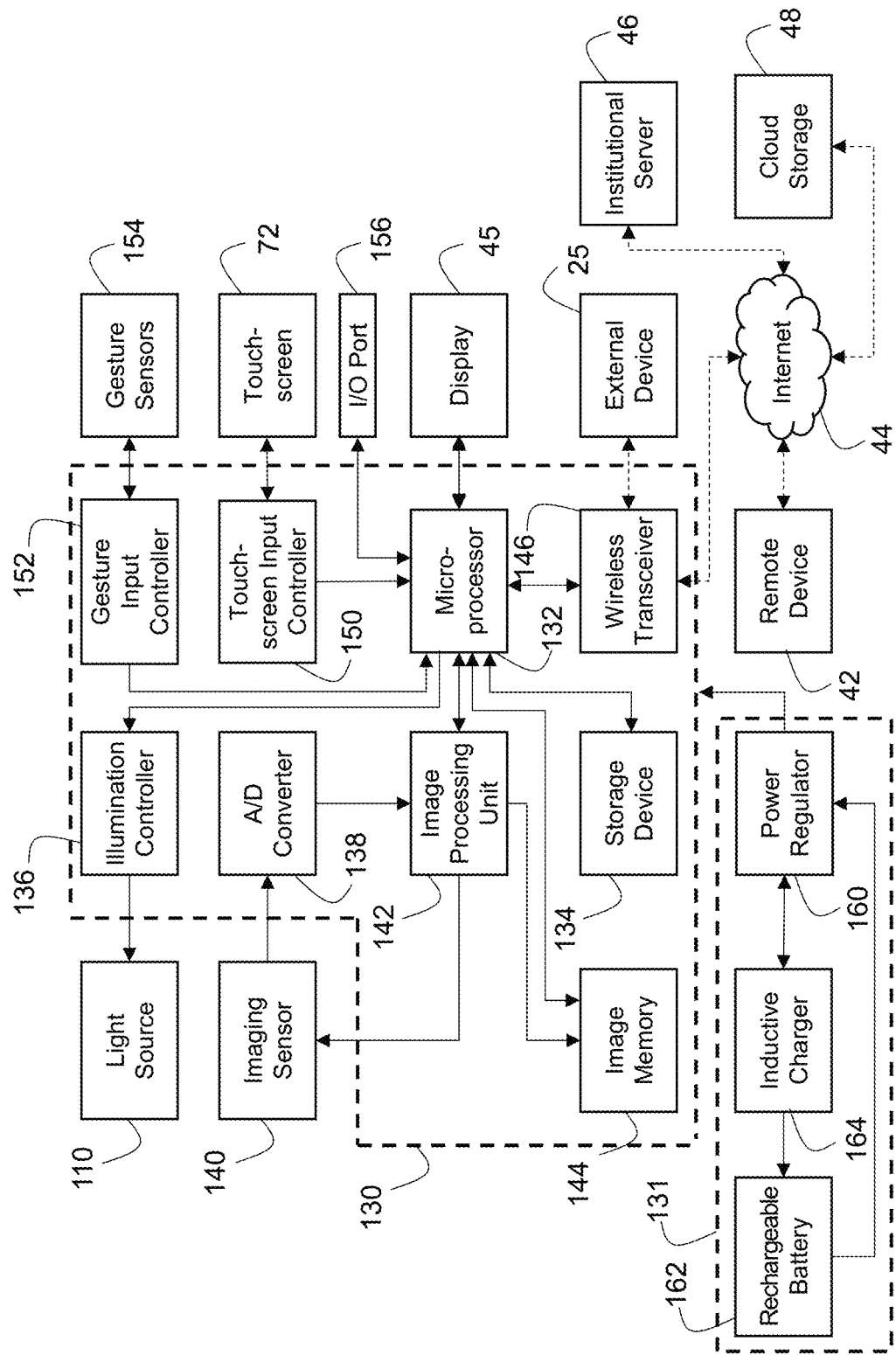
FIG. 9 is a block diagram of a wiring diagram of a wireless imaging unit according to an embodiment of this disclosure.

With reference to embodiments of FIGS. 8 and 9, the housing 90 of the wireless imaging unit 20 may or may not be a hermetically sealed enclosure. The housing is designed to protect a number of internal components including the touchscreen display unit 72, a plurality of control PCBs 120, a plurality of mounting standoffs 122 which secure the control PCBs 120 within the housing, and at least one thermal heatsink 124. The standoffs 122 and heatsinks 124 are thermally coupled to the PCBs 120 and the housing 90 in order to draw or dissipate heat away from the internal electronic circuitry towards the housing 90.

The PCBs 120 includes a number of electronic circuitry components which control and power the wireless imaging unit 20, as depicted in FIG. 9. The electronic circuitry included on at least one of the PCBs 120 is including in a system controller 130 and a power controller 131. The system controller 130 includes a plurality of circuit components that are responsible for controlling aspects the imaging device 20. The system controller 130 includes a microprocessor 132, which interfaces with a number of electronic components to send and receive instructions to control various aspects of the imaging unit 20 functions. The system controller 130 includes a storage device 134 which is a memory device such as a computer readable storage medium, such as transistor memory or others, such as cache memory, flash memory, or others, for program instructions to be executed by the microprocessor 132. In addition to program instructions, the storage device 134 can store EMR related data such patient and procedure data. The system controller 130 also includes an illumination controller 136 which receives instructions from the microprocessor 132 to adjust an intensity or brightness of an incident light from the light source 110 as well as a frequency component or components of the incident light.

An analog-to-digital converter (ADC) 138 receives analog signals from an imaging sensor 140 and converts the analog signal to a digital signal, which can then be post-processed by an image processing unit 142. The type of imaging sensor 140 can be selected from complementary metal-oxide-semiconductor (CMOS), charge coupled device (CCD), or other imaging sensor devices developed in future but not yet contemplated. The image processing unit 142 is capable of performing a number of image processing and post processing techniques in real-time or substantially real-time on captured digital images or videos. Examples of image processing techniques include edge detection, objection detection, geometric transformations, perspective correction, color correction, color calibration, motion compensation, data compression, noise reduction, filtering, or others. The image processing unit 142 is also capable of controlling a functionality of the imaging sensor 140, such as adjusting a focal depth by controlling an integrated autofocus mechanism, pixel clock, sensitivity, offset, signal amplification, gain, gamma, or others. The image processing unit 142 is capable or adjust an image size that is displayed on an external or remote device 25, 42 due to difference in screen resolution or aspect ratio between devices. Another feature of the image processing unit 142 is to automatically align various captured images such that the captured images are centered in a display independent of a size, aspect ratio, or resolution of the display being used whether the display is the local display 72, a display of an external device 25, or a display of a remote device 42. The image processing unit 142 receives a set of display information from the microprocessor 132 and formats an output image correspondingly. Post-processed images can then be stored on an image memory 144 for later retrieval to be viewed locally on the touchscreen display 72, externally on an external device 25 via direct wireless connection or over the local network 50, or remotely on a remote device connected via an Internet connection 44.

The system controller 130 includes at least one wireless transceivers for connecting the wireless imaging unit 20 to a local network via a wireless access point 52, directly to an external device using a peer-to-peer direct connection, such as Wi-Fi Direct. In another embodiment, the system controller 130 includes 20 or more wireless transceivers 146 in order for the wireless imaging unit 20 to maintain more than one simultaneous or substantially simultaneous wireless data connection. For example, the system controller 130 can stream image data during an endoscopic procedure to two or more external devices 25, remote devices 42, institutional servers 46, cloud storage systems 48, and any combination thereof.

The system controller 130 also includes a number of input controllers, such as a touchscreen input controller 150 and a gesture input controller 152. The touchscreen controller 150 receive a user's touch input data from the touchscreen display unit 72 which permits the user to input data onto the storage device 134 or control an operation of the wireless imaging unit 20. For example, a user can input metadata regarding a stored image or video pertaining to an endoscopic procedure, user can also use the touchscreen to access and populate 1 data into the display 72 regarding an upcoming endoscopic procedure, the user can authorize access for an external or remote device 25, 42 to remotely view an endoscopic procedure in real-time or substantially real-time. The gesture controller 152 receives gesture input data from at least one gesture sensor 154, such as a motion sensor like a gyroscope or accelerometer, a photo-sensor, a radar antenna, or a microphone. By detecting gesture data from a user, the system controller 130 can be controlled without direct input from a user to adjust light source frequency or intensity, control image capture, or the like using gestures such as those detected by a motion sensor detecting motion of the imaging unit 20; a radar antenna can capture touchless user hand motions and detect gestures therefrom in order establish interactions with the imaging unit 20 without direct touch; a microphone can detect voice controls; and other gesture sensors and gesture types not yet contemplate.

The system controller 130 also includes an input-output (I/O) data transfer port 156 capable of transfer of digital data to an external device, such as a personal computer, smartphone, tablet, or the like using a convention Universal Serial Bus (USB) interface. The I/O port 156 is also capable of powering the imaging unit 20.

The power controller 131 provides power to various electronic components of the imaging unit 20, such as the imaging sensor 140, the light source 110, the system controller 130, the display unit 72, or others. The power controller 131 includes a power regulator 160, which receives power from the I/O port 156 or an internal rechargeable battery 162. The power regulator 160 regulates the voltage and/or current which is the supplied to such electronic components. The power regulator 160 also regulates a recharging of the rechargeable battery 162. As previously mentioned, the I/O port 156 is capable of supplying power to the imaging unit 20 as well as providing power to recharge the battery 162. The power controller 131 also includes an inductive charging element 164 which can also supply power to recharge the battery 162. The docking station 26 may also include a complementary inductive charging element to transit is wireless charging signal to the inductive charging element 164. Thus, by placing the wireless imaging unit 20 on top of the docking station 26, a charging cycle will commence which will in turn charge the battery 162, which can be internal. The rechargeable battery 162 maybe a conventional lithium-ion type rechargeable battery, but other battery types and chemistries are also contemplated. In some embodiments, the power controller 131 includes a wireless charging element which also supply power to recharge the battery 162, with the wireless charging element being radiofrequency based, optically based, acoustically based, or others. As such, the wireless image unit 20 can be used without placement on top of the docking station 26, yet still be recharging.

Figure 10:
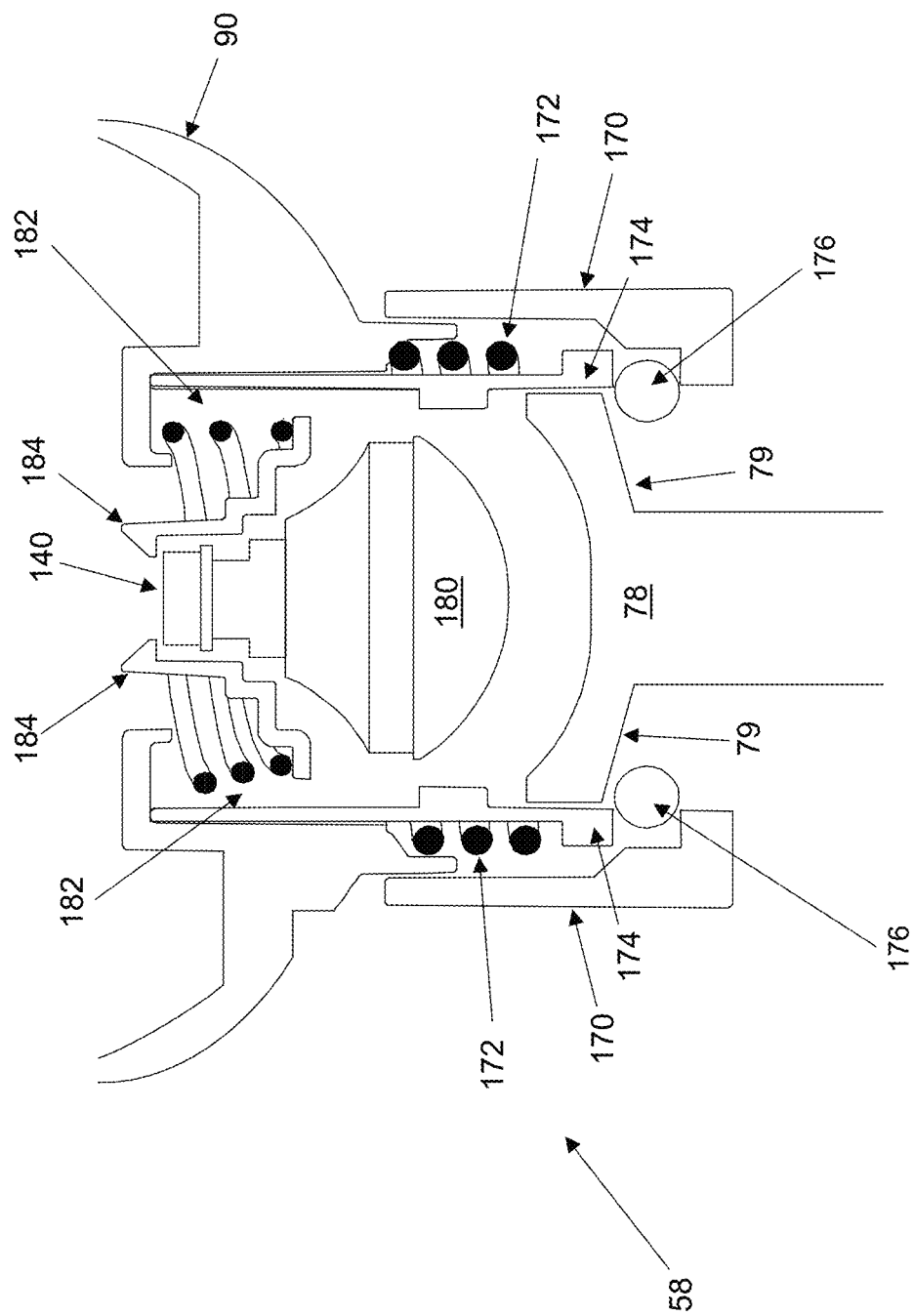
FIG. 10 is a cross-sectional view of a variable coupling system according to an embodiment of this disclosure.

With reference to an embodiment of FIG. 10, a cut-away view of the variable clamping system 58 is depicted. The variable coupling system 58 mechanically couples the wireless imaging unit 20 to the flange 79 of the eyepiece 78 through an opening at the distal end 92 of the imaging unit 20. As previously mentioned, the flange 79 angle, diameter, and/or thickness can vary amongst manufactures of endoscopes 12; therefore, the clamping system 58 is capable of securing the eyepiece 78 and imaging unit 20 together independent of these variations in the flange 79 thickness, diameter, and/or angle. To accomplish this, the clamping mechanism 58 includes a bearing lock coupling in which an outer sleeve 170 which is loaded by a spring 172 in between the outer sleeve 170 and an inner sleeve 174. The inner sleeve 170 includes a plurality of roller bearings 176 disposed in a corresponding number of tapered holes of receptacles. The outer sleeve 170 is normally in a relaxed state which engages the roller bearings 176 to locked state in which the roller bearings 176 are forced or pushed inwards towards an opening which accepts the eyepiece 78. This effectively decreases a diameter of the opening, which ensures that the eyepiece 78 remains locked in the coupling mechanism 58. To disengage the roller bearings 176, the outer sleeve 170 can be translated bi-directionally in a lateral direction, in other words pushed or pulled from the relaxed state, to selectively disengage the roller bearing 176. When disengaged, the roller bearings 176 retreat outward away from the opening into the receptacles of the inner sleeve 174. This arrangement allows the user to either push or pull the outer sleeve 170 to release the roller bearings 176 to either insert the eyepiece 78 into the opening or remove the eyepiece 78 from the opening. This arrangement also allows for a eyepieces of varying diameter to be secured within the clamping mechanism 58. By having the opening slightly larger than the industry standard of 31.75 mm, such as an opening 32-35 mm in diameter, and having the roller bearings 176 extend into the opening at least 4-8 mm, the clamping mechanism 58 can accept and secure eyepieces over a range of 30-35 mm.

To account for variable thickness in the eyepiece flange 79, the imaging sensor 140 and corresponding optics 180 are biased directly against the eyepiece 78 independent of the thickness of the flange 79. A biasing member or spring 182 acts against a mounting bracket 184, which secures the imaging sensor 140 and the optics 180, laterally towards the eyepiece 78 to ensure that the imaging sensor 140 and the corresponding optics 180 are secured directly against the eyepiece 78. The imaging sensor 140, the imaging optics 180, the biasing member 182, and the mounting bracket 184 are all disposed within the inner sleeve 174 of the variable clamping system 58. In this arrangement, the imaging sensor 140, the imaging optics 180, and the mounting bracket 184 can translate laterally and independently of the housing 90 of the imaging unit 20 allowing for the wireless imaging unit 20 to accept eyepieces 79 with varying flange 79 thicknesses.

Figure 11B:
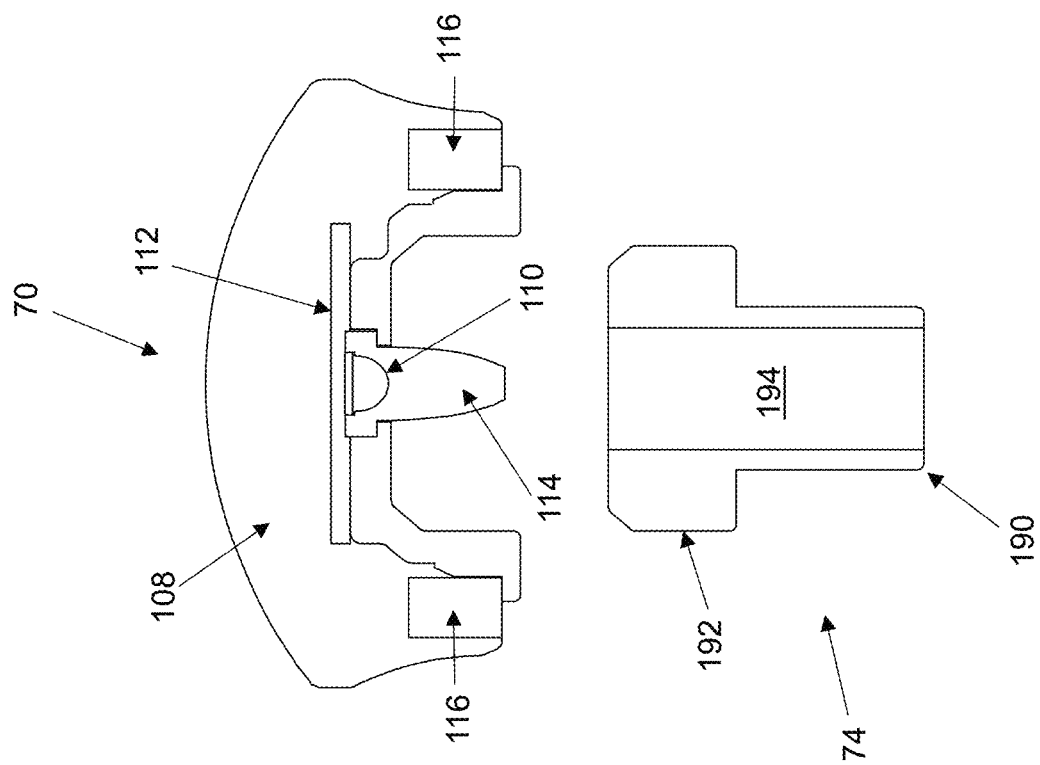
FIGS. 11A-11B is a schematic view and a cross-sectional view of a light source assembly and associated light port adapter according to an embodiment of this disclosure.
Figure 11A:
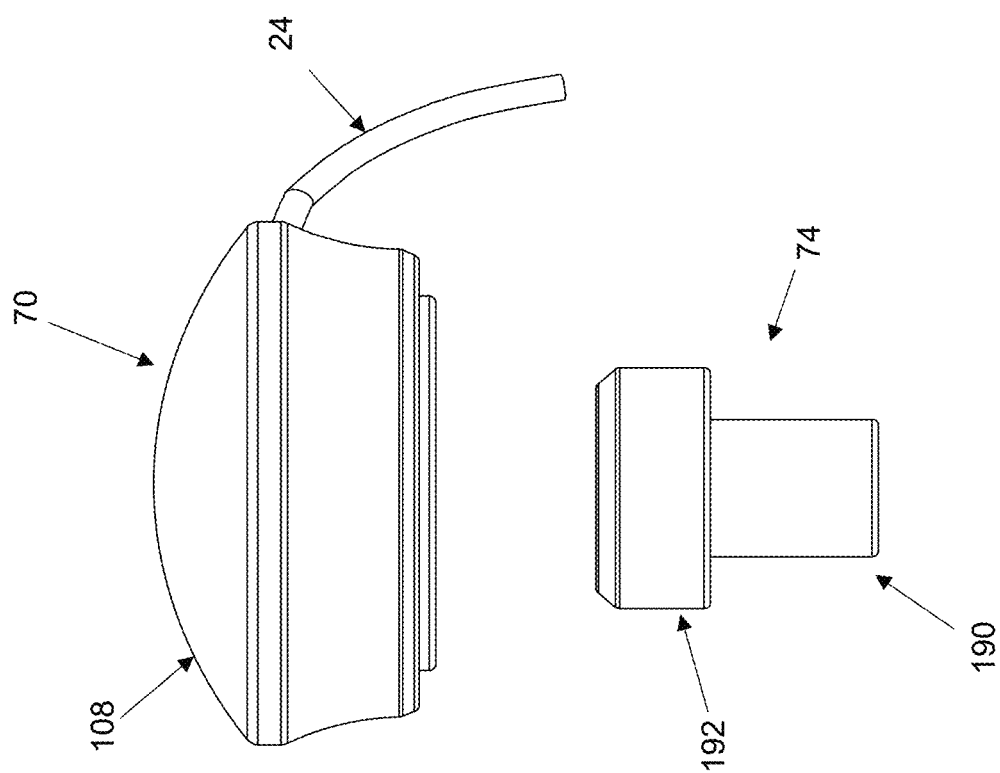

With reference to embodiments of FIGS. 11A and 11B, a cut-away view of the light source assembly 70 and the light port adapter 74 is depicted. As previously mentioned, the light source assembly 70 includes a housing 108, which acts as a heatsink to draw heat away from the light source 110 and the light source PCB 112. Disposed within the housing 108 is a ferromagnetic ring 116 which maybe in a continuous ring of a ferromagnetic material or a plurality of discrete ferromagnetic elements. The light port adapter 74 has a base 190, which attaches to the light port 68 and a top 192, which is composed of ferritic materials so as to magnetically couple with the ferromagnetic ring 116. The light port adapter 74 defines a central shaft 194 which accepts the light port 68 in a number of mechanical fastening fashions. For example, the central shaft 194 can include a female helical thread pattern to complement a male helical thread pattern found on a light port 68 of the endoscope 12. However, other mechanical or engineered fittings are also contemplated such an interference fit and the like.

Figure 12:
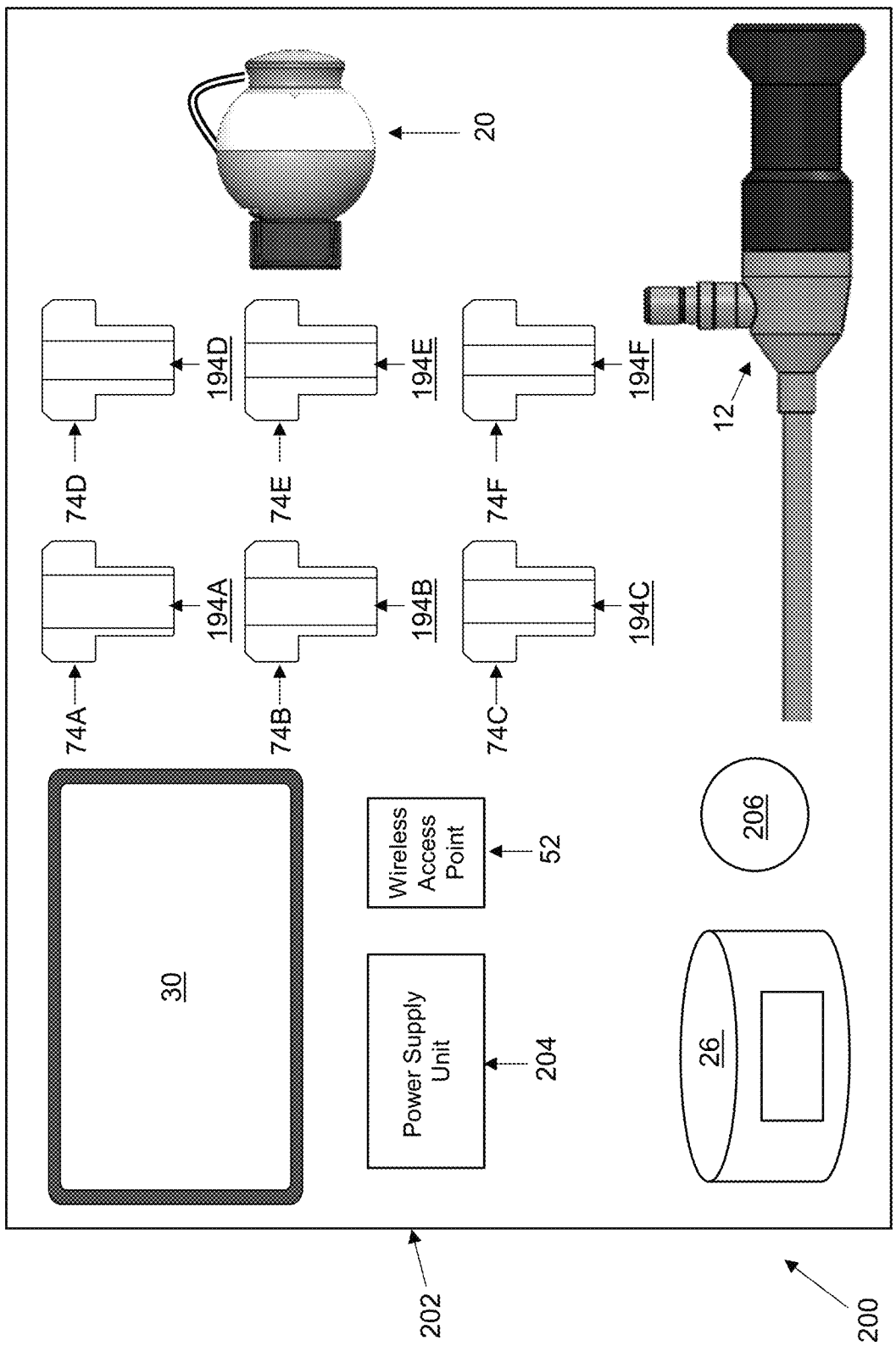
FIG. 12 is a structural diagram of a kit for portable endoscopic inspection system according to an embodiment of this disclosure.

With reference to an embodiment of FIG. 12, a portable endoscopic inspection kit 200 for producing endoscopic images of a region of interest is presented. The kit 200 includes a carrying case 202, which houses in a secure manner a set of contents of the kit 200 as well as being particularly adapted for travel to remote locations in which electrical and wireless internet connections are not readily available. The kit 200 includes (i) an endoscope 12 for transmitting incident light to a region of interest 16 and receiving the reflected light therefrom in the form of images; (ii) a wireless imaging unit 20 for recording the reflected images from the region of interest 16; (iii) a plurality of light port adapters 74A-74F each of which varies according to its respective central shaft 194A-194F in order to accommodate a plurality of light ports 68 geometries; (iv) a wireless access point for wirelessly receiving recorded images from the imaging unit 20 and wirelessly transmitting the receiving images to an external device 25; (v) an external device 25, such as a docking station 26 and/or an external display device 30 for displaying the recorded images; and (vi) a power supply unit 204 which includes a rechargeable battery that supplies power to the various components, such as recharging the imaging unit 20, the wireless access point 52, the docking station 26, the display device 30, and an accessory port 206 for providing power to an external device and receiving power to charge the rechargeable battery or to directly supply power to the various components of the kit 200.

As previously stated, endoscopes from various manufactures vary in size and shape of its respective light port and eyepiece flange. Therefore, in order to accommodate light ports with varying dimensions, the kit 200 includes a plurality of light port adapters 74A-74F each of which varies according to its respective central shaft 194A-194F. For example, a central shaft 194A-194F may vary in major or minor diameter, thread density, thread pitch, or others.

The kit 200 allows a practitioner or a user to travel to remote areas where no electricity if available. For example, while travelling in a vehicle, the accessory port 206 can be plugged into a DC power port in the vehicle to recharge the rechargeable battery of the power supply 204. Upon reaching their destination, the practitioner or the user can examine patients without being burdened by wires for power, data transfer, and/or display. One can appreciate that the kit 200 may include other accessories which useful to a practitioner in order to perform an endoscopic inspection. In some embodiments, the kit 200 includes a renewable energy source, such as a photovoltaic array, a wind turbine, or others, configured for electrical or mechanical coupling with the accessory port 206.

Figure 13:
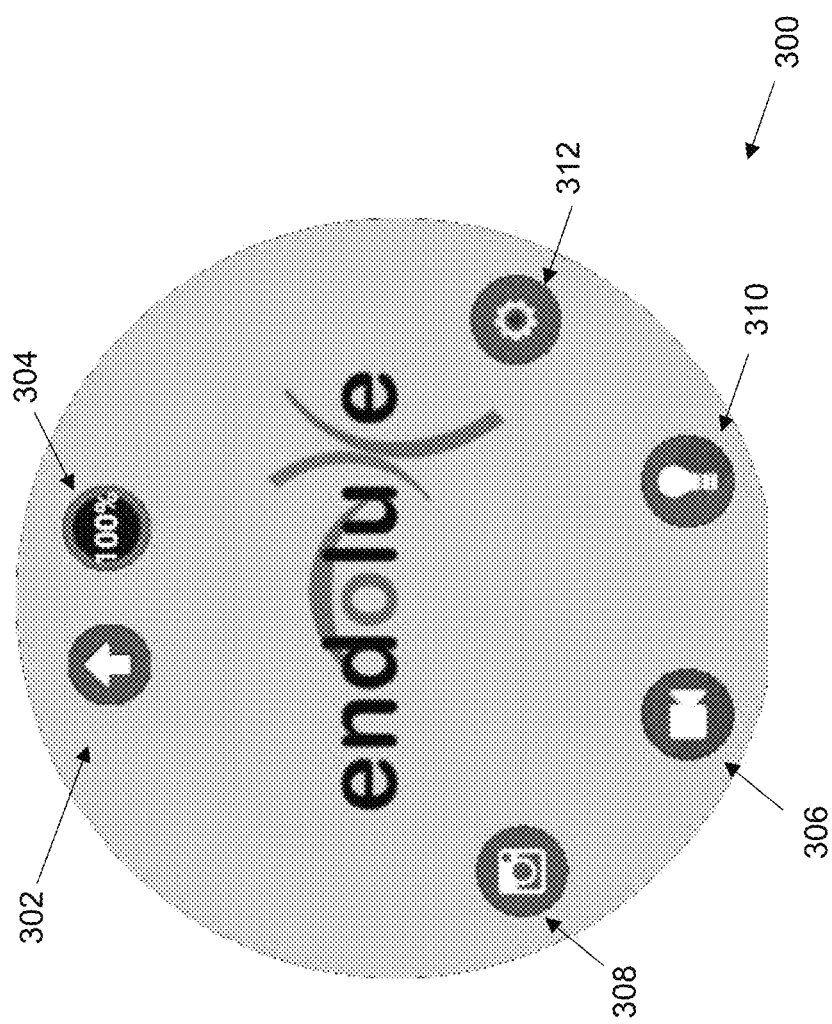
FIG. 13 is an example of a user interface for a wireless imaging unit according to an embodiment of this disclosure.
Figure 14A:
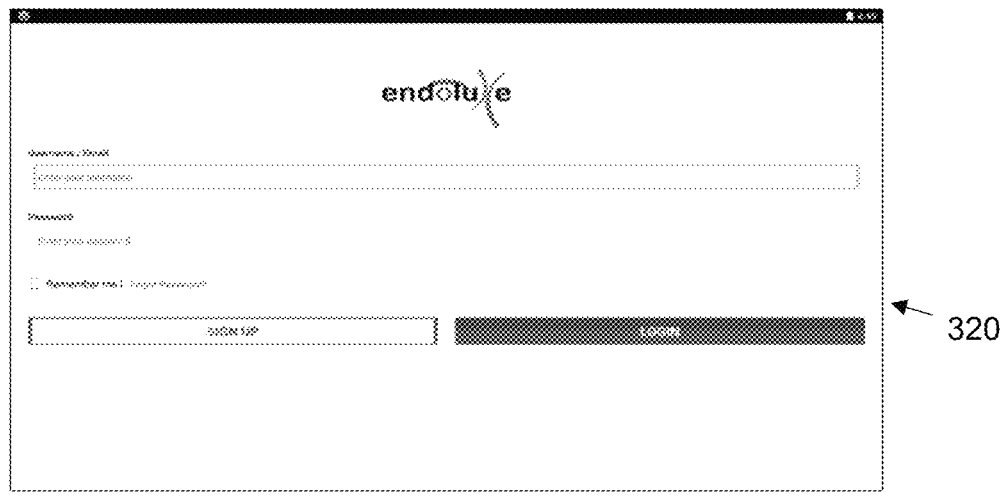
FIGS. 14A-14H are various examples of user interfaces for an external device according to an embodiment of this disclosure.
Figure 14B:
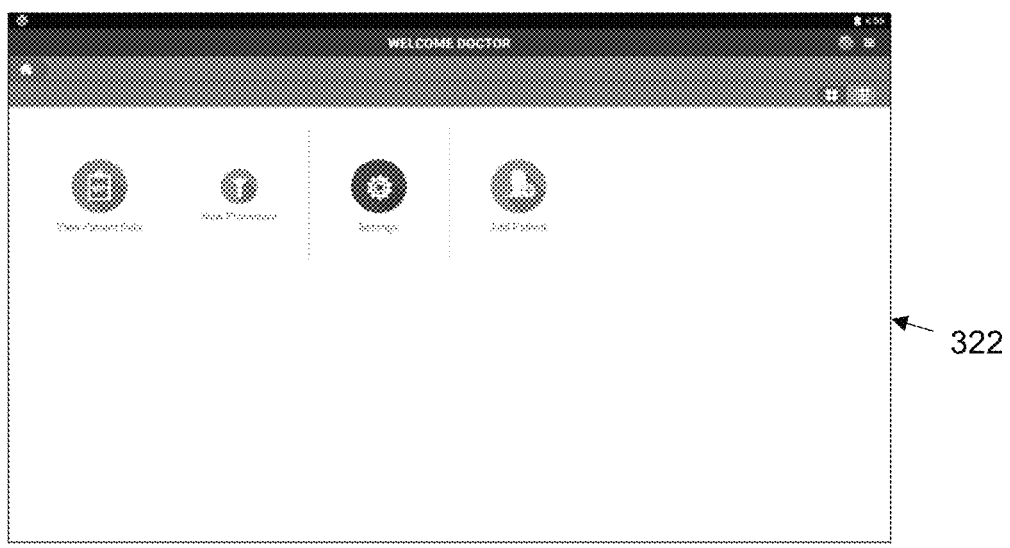
Figure 14C:
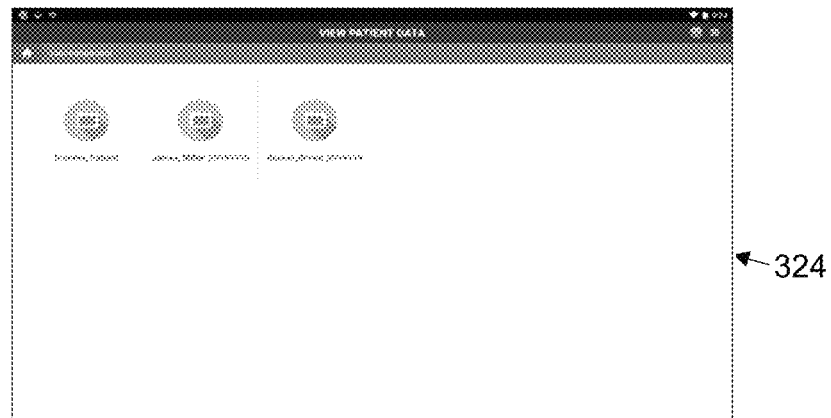
Figure 14D:
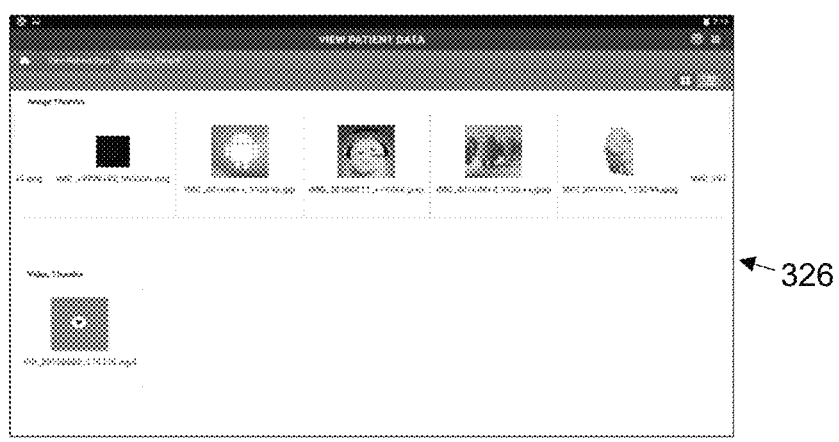
Figure 14E:
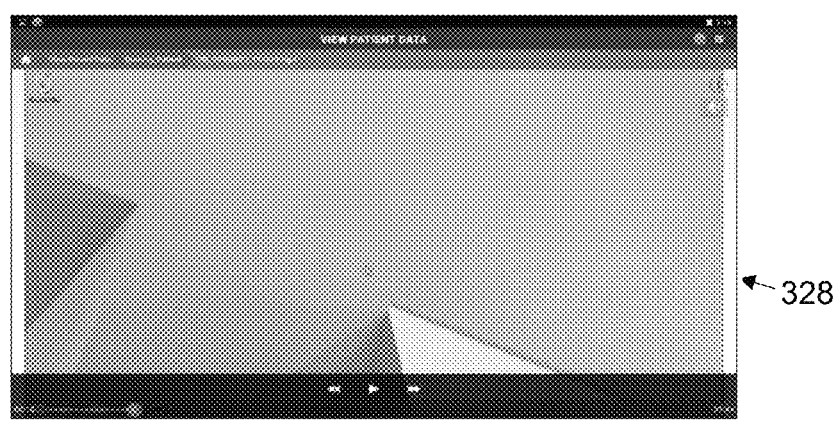
Figure 14F:
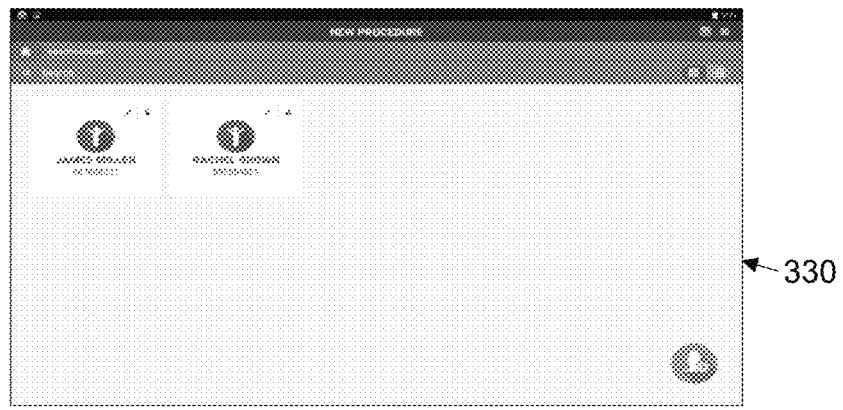
Figure 14G:
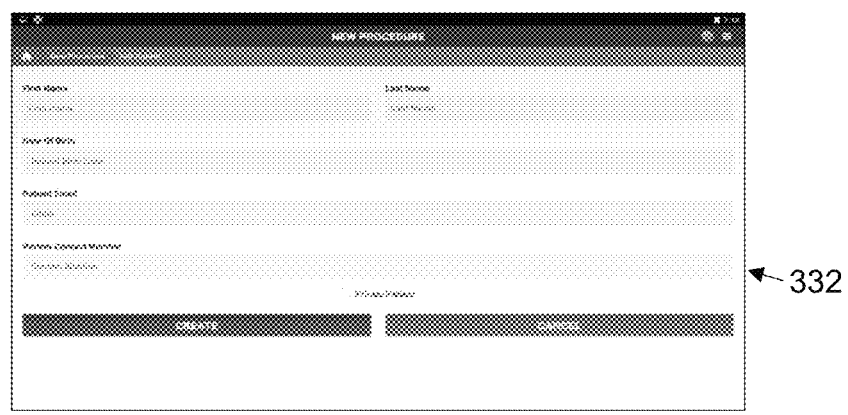
Figure 14H:
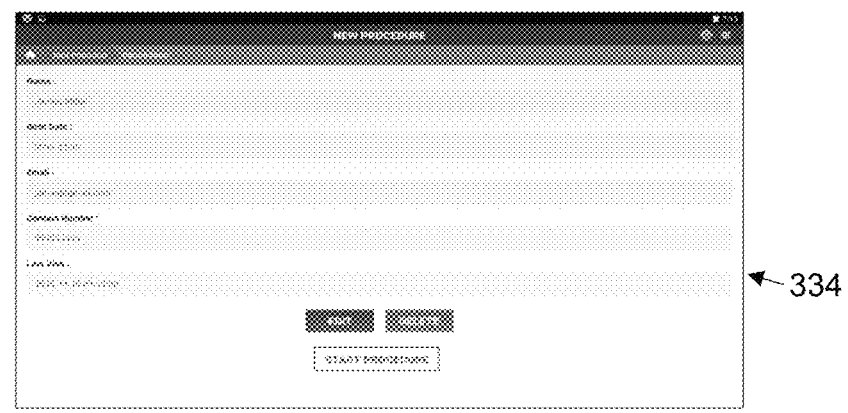

With reference to an embodiment of FIG. 13, the wireless imaging unit 20 includes a user interface 300, which allows a user to control the device in order to adjust, control, display, process, transfer, store, and retrieve recorded image data and/or EMR data. The user interface 300 is typically displayed on the touchscreen display unit 72, but can also be displayed on an external device 25 directly via the I/O port 156 or wirelessly via the transceiver 146. A user interacts with the imaging unit 20 using a variety of inputs which can take the form of (i) directly interacting with the touchscreen 72; (ii) using a remote control, such as a wireless joystick, a gamepad, a wireless control panel, or a remote function using a smart device authorized with the imaging unit 20; (iii) using gestures that are sensed by the gesture sensors 154 and then interpreted by the gesture controller 152; (iv) and other input methods not yet contemplated.

Once the imaging unit 20 is powered up, the user interface 300 is presented to the user on the display 72. The user interface 300 includes a number of indicators and/or buttons to relay information regarding a state of the imaging unit 20 to the user. The user interface 300 includes a connection status indicator 302 which has four states, each of which is denoted by a different icon for the indicator: a disconnected state in which the imaging unit 20 is not connected to any external devices 25, a searching state in which the imaging unit 20 is searching for available external devices 25 connected to the network 50, a connected state in which the imaging unit 20 is currently connected to at least one external device 25, and a casting state in which the imaging unit 20 has successfully established a connection with an external device 25 and is currently transmitting the recorded images in real time to the connected device 25. A user can interact with the connection status indicator 302 by pressing an icon in order to cycle through any one of the connections states.

Other indicators or buttons includes a battery status indicator 304, which shows the rechargeable battery 162 level in a form of a percentage; a video record button 306, when depressed, will initiate storing the image data from the imaging sensor 140 as a time series of images or a video to the local image memory 144, an external device 25, a remote device 42, institutional server 46, cloud storage 48, or others; an image capture button 308, when depressed, will initiate storing a still image from the imaging sensor 140; a light control button 310 which can control the intensity and/or frequency of the incident light from the light source 110; and a settings button 312, when depressed, will display verbose information about imaging unit 20.

With reference to embodiments of FIGS. 14A-14H, the portable endoscopic system 10 includes a user interface for the external device 25. When first launching the user interface on the external device 25, a user will be prompted by a log in screen 320 to log into an application or software using personal credentials in order to access features of the system 10, such as via passwords, biometrics, multi factor authentication, or others. Once the user is logged into the software, the user is presented with a welcome screen 322 which allows the user to access Settings, View Patient Data, initiate a New Procedure, Add a Patient, and the like. From the View Patient Data screen 324, the user can select a patient data file from a list of individual patient data files, each of which is associated with respective EMR data. Once a specific is selected, a patient is presented with a media screen 326 which displays a list of images and videos that are associated with the respective patient. From there, the user can view endoscopy images and play video by clicking on the specific file, users can also zoom in/zoom out images, users can edit image with drawing on image with finger touch and add caption on double tap of image, users can play and control endoscopy videos using standard play, pause, forward and backward playback of the video 328.

From the New Procedure Screen 330, a user can initiate patient's endoscopy procedure and also view, edit, or delete individual patients. To start new procedure for patient, the user will click on the patient and a New Procedure Input screen 332 will prompt a user to input patient data or fill in missing data. Once the patent information is complete, an option to Start New Procedure 334 will be presented to the user.

From the Settings Screen, a user is presented with options and information regarding the imaging unit 20. For example, the user can adjust network settings such as wireless transceiver 146 connectivity to wireless access points 52. Other settings include: About settings, Device Info, Subscription Info, Time & Date, Clinical Provider, Help, Register Institute, Contact Us, User Info, Restore Patient Data, Firmware Upgrade, and the like.

Figure 15:
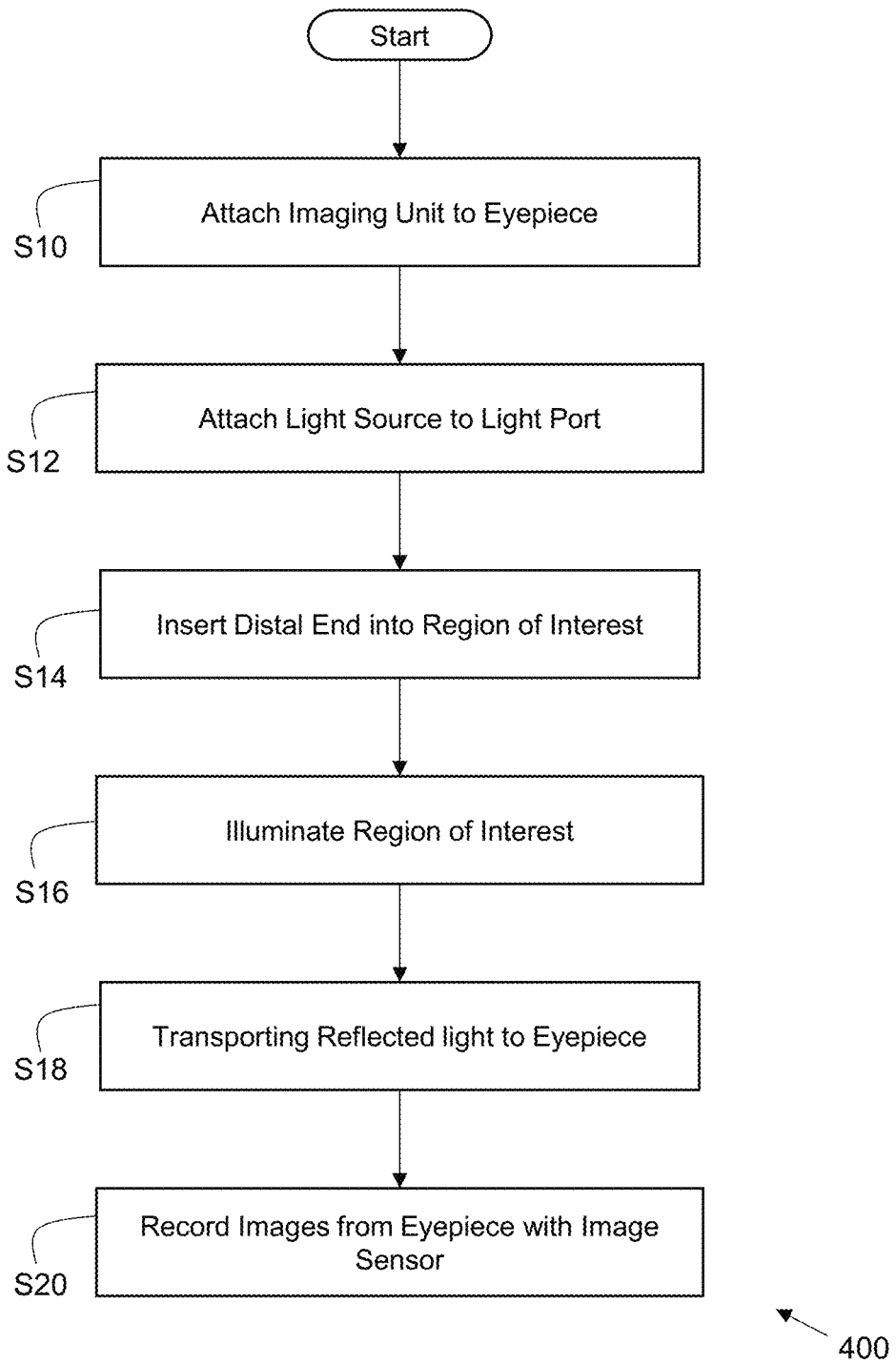
FIG. 15 is flowchart detailing a method for performing an endoscopic examination according to an embodiment of this disclosure.

With reference to an embodiment of FIG. 15, a method for performing an endoscopic examination 400 includes a step S10 of attaching the wireless imaging unit 20 to a flanged eyepiece 78 of the endoscope 12 with a variable coupling system 58 which mechanically couples the imaging sensor 140 to the flanged eyepiece 78 independent of flange shape and size. A step S12 includes attaching the light source assembly 70 to the light port 68 of the endoscope 12. The light port 68 receives an incident light generated by the light source assembly 70. A step S14 includes inserting the distal end 60 of the endoscope 12 into the region interest 16 of a patient. A step S16 includes transporting the incident light from the light port 68 along an illumination pathway to the lens assembly 80 housed within the distal end 60 of the endoscope 12. A step S18 includes transporting reflected light from the region of interest 16 with the lens assembly 80 along an imaging pathway to the flanged eyepiece 78. A step S20 includes recording images from the flanged eyepiece 78 with the imaging sensor 140 of the wireless imaging unit 20.

Although this disclosure has been described in some detail for purposes of clarity, a skilled artisan will realize that certain changes and modifications may be made without departing from principles thereof. One should note that there are many alternative ways of implementing systems, devices, and methods described herein. Accordingly, various embodiments of this disclosure are to be considered as illustrative and not restrictive, and this disclosure is not to be limited to various details given herein, which may be modified within scope and equivalents of appended claims.

What is claimed is:

1. A portable endoscopic inspection system comprising: an endoscope having a proximal end with a flanged eyepiece for observation and a handle, a distal end for insertion into a region of interest, a lens assembly housed within the distal end, a light port, an illumination pathway which optically couples the light port and the lens assembly to transport incident light to the region of interest, and an imaging pathway which optically couples the eyepiece and lens assembly for transporting the reflected light from the region of interest to the flanged eyepiece; and a wireless imaging unit comprising a housing, a light source assembly detachably coupled to the light port for generating the incident light when the light source assembly is in an undocked state relative to the display unit, an imaging sensor for recording images of the reflected light from the eyepiece, a wireless transceiver for wirelessly transmitting the images, a battery, an inductive charging element for recharging the battery, a display unit powered by the battery, and a variable coupling system which mechanically couples the imaging sensor to the flanged eyepiece independent of the shape and/or size of the flange, wherein the housing houses the imaging sensor, the wireless transceiver, the battery, the inductive charging element, and the display unit, wherein the light source assembly covers the display unit when the light source assembly is in a docked state.

2. The portable endoscopic inspection system according to claim 1, wherein the variable coupling system comprises:
    sensor optics which focuses the reflected light from the flanged eyepiece onto the imaging sensor; and
    a biasing member which biases the sensor optics directly against the eyepiece.

3. The portable endoscopic inspection system according to claim 2, wherein the variable coupling system further includes:
    at least one circumferential roller bearing which mechanically engages the flanged eyepiece to the variable coupling system in order to directly couple the sensor optics with the flanged eyepiece; and
    an outer sleeve which translates bi-directionally in a lateral direction to selectively disengage the roller bearing from the flanged eyepiece.

4. The portable endoscopic inspection system according to claim 3, wherein the outer sleeve surrounds the sensor optics and imaging sensor.

5. The portable endoscopic inspection system according to claim 3, wherein the roller bearing generates an engagement force opposite to the biasing member in order to axially align the sensor lens and the eyepiece.

6. The portable endoscopic inspection system according to claim 3, wherein the eyepiece flange has a major width of 30 mm to 40 mm.

7. The portable endoscopic inspection system according to claim 1, wherein the wireless imaging unit further comprises a recess in the housing for magnetically receiving the light source assembly.

8. The portable endoscopic inspection system according to claim 1, wherein the wireless imaging unit further comprises a ferromagnetic adapter which attaches to the light port and magnetically couple the light source assembly to the light port.

9. The portable endoscopic inspection system according to claim 1, wherein the light source assembly further includes a heat sink to dissipate heat away from a light source.

10. The portable endoscopic inspection system according to claim 1, wherein the light source assembly further comprises:
a multispectral light source; and
a light guide which optically couples the light source to the illumination pathway.

11. The portable endoscopic inspection system according to claim 10, wherein the multispectral light source includes a plurality of light emitting diodes, each capable of outputting a selected wavelength.

12. The portable endoscopic inspection system according to claim 10, wherein the multispectral light source is capable of at least one of narrow band imaging, auto-fluorescence imaging, and white light imaging.

13. The portable endoscopic inspection system according to claim 10, wherein the multispectral light source is capable of selectively outputting a range of wavelengths from 365 nm to 540 nm.

14. The portable endoscopic inspection system according to claim 1, wherein the battery powers the wireless transceiver for wirelessly transmitting the recorded images.

15. The portable endoscopic inspection system according claim 1, wherein the wireless imaging unit further includes at least two wireless transceivers for wirelessly transmitting the recorded images from each wireless transceiver substantially simultaneously.

16. The portable endoscopic inspection system according to claim 1, further comprising a cable connecting the housing and the light source assembly.

17. The portable endoscopic inspection system according to claim 1, further comprising a docking station with at least one wireless receiver for receiving the wirelessly transmitted recorded images.

18. The portable endoscopic inspection system according to claim 17, wherein the docking station further includes an inductive element for wirelessly transmitting power to the battery through the inductive charging element.

19. The portable endoscopic inspection system according to claim 17, wherein the display unit is a first display unit, wherein the docking station further includes a video output port for transmitting wirelessly received images to a second display unit.

20. The portable endoscopic inspection system according to claim 1, wherein the wireless imaging unit further includes:
an image control unit which controls:
(a) the image sensor to record the images from the eyepiece and
(b) the light source assembly to produce the incident light which illuminates the region of interest.

21. The portable endoscopic inspection system according to claim 20, wherein the image control unit controls an autofocus driver to adjust the focal length between the imaging sensor and the sensor optics.

22. The portable endoscopic inspection system according to claim 1, wherein the wireless imaging unit further includes:
an image processing unit which receives analog signals from individual pixels of the imaging sensor which correspond to the recorded images,
converts the analog signals to digital signals, and
stores a corresponding digital image to an image memory.

23. The portable endoscopic inspection system according to claim 22, wherein the image processing unit comprises:
an image enhancement unit which adjusts individual pixels values of the stored digital image according a selected image processing algorithm.

24. The portable endoscopic inspection system according to claim 23, wherein the image processing algorithm is selected from color enhancement, greyscale enhancement, contour enhancement, pattern recognition, feature extraction, digital filtering, and any combination thereof.

25. The portable endoscopic inspection system according to claim 22, wherein the image processing unit comprises:
a post-processing unit which encodes the stored digital images for wireless transmission.

26. The portable endoscopic inspection system according to claim 1, further comprising an elongated flexible tube extending from the handle to the distal end which houses the at least the imaging pathway and the illumination pathway.

* * * * *